United States Patent [19]

Ueda et al.

[11] Patent Number: 5,340,725
[45] Date of Patent: Aug. 23, 1994

[54] EXPRESSION VECTOR FOR INSULIN-LIKE GROWTH FACTOR I AND METHOD OF PRODUCTION

[75] Inventors: Ikuo Ueda, Osaka; Mineo Niwa, Kyoto; Yoshimasa Saito; Yoshinori Ishii, both of Osaka; Tadashi Hitaguchi, Hyogo, all of Japan

[73] Assignee: Fujisawa Pharmaceutical Co., Ltd., Osaka, Japan

[21] Appl. No.: 13,204

[22] Filed: Feb. 1, 1993

Related U.S. Application Data

[63] Continuation of Ser. No. 488,459, Feb. 26, 1990, abandoned, which is a continuation of Ser. No. 105,180, Oct. 6, 1987, abandoned.

[30] Foreign Application Priority Data

Oct. 9, 1986 [JP] Japan ................. 61-240702

[51] Int. Cl.$^5$ ............... C12N 15/00; C12N 5/00
[52] U.S. Cl. ................... 435/69.4; 435/69.1; 435/172.3; 435/252.3; 435/252.33; 435/320.1; 536/23.5
[58] Field of Search .............. 536/23.5; 435/69.1, 435/69.4, 320.1, 172.3, 252.3, 252.33

[56] References Cited

U.S. PATENT DOCUMENTS

| | | | |
|---|---|---|---|
| 4,366,246 | 12/1982 | Riggs | 435/68 |
| 4,673,641 | 6/1987 | George et al. | 435/68 |
| 5,019,500 | 5/1991 | Ueda et al. | 435/69.1 |
| 5,028,531 | 7/1991 | Ueda et al. | 435/69.4 |

FOREIGN PATENT DOCUMENTS

| | | |
|---|---|---|
| 0155655 | 9/1985 | European Pat. Off. . |
| 0206769 | 6/1986 | European Pat. Off. . |
| 8605804 | 10/1986 | World Int. Prop. O. . |

OTHER PUBLICATIONS

Nilsson et al *Nucl Acids Res* vol. 13(4) pp. 1151–1163 Mar. 1985 "Efficient Secretion and Purification of Human Insulin–Like Growth Factor I With a Gene Fusirinvector in *Styphlococcos*".
Schnoer *Proc Natl Acad Sci* vol. 81 pp. 5403–5407 1987.
Schoo et al *Chem Abst* vol. 104 No. 201575f 1986 "Preparation of a Fusion Protein Comprising Human γ-Interferon at Human Interleukin-2 in *Escherichia coli*".
Proc. Natl. Acad. Sci. USA, vol. 81, Sep. 1984, pp. 5403–5407; B. E. Schoner et al.: "Role of mRNA translational efficiency in bovine growth hormone expression in *Echerichia coli*" *Whole Article*.
J. Biochem, vol. 101, No. 5, 1987, pp. 1281–1288; Y. Saito et al.: "Direct expression of a synthetic somatostatin C gene in *Escherichia coli* by use of a two-cistron system" *Whole Article*.
Lewin, B., *Genes*, John Wiley and Sons, Inc., New York (1983), p. 302.
Glover, D. M., *Gene Cloning*, Chapman & Hall, New York (1986), pp. 21–25.
Sigma Chemical Co. Catalog (1989), pp. 1014 and 1019.

*Primary Examiner*—Robert J. Hill, Jr.
*Assistant Examiner*—Marianne Porta Allen
*Attorney, Agent, or Firm*—Oblon, Spivak, McClelland, Maier & Neustadt

[57] ABSTRACT

Two-cistronic Met-IGF-I expression vector, in which the first cistron encodes a protective peptide with a molecular weight of about 500–50,000 and the second cistron encodes IGF-I, was provided. Also provided is a process for preparing Met-IGF-I, which comprises transforming *E. coli* with said vector and growing the resultant transformant, followed by the lysis of the cell culture and isolation of Met-IGF-I.

10 Claims, 24 Drawing Sheets

Fig. 1

```
                                                    1
                        EcoRI   Met  Gly  Pro  Glu  Thr  Leu
                  5'- AATTC - ATG - GGT - CCT - GAA - ACT - CTG -
                  3'- G -     TAC - CCA - GGA - CTT - TGA - GAC -
```

```
                 10
Cys  Gly  Ala  Glu  Leu  Val  Asp  Ala  Leu  Gln  Phe  Val  Cys  Gly
TGC- GGC- GCT- GAA- CTG- GTT- GAC- CCT- CTG- CAA- TTT- GTA- TGT- GGT-
ACG- CCG- CGA- CTT- GAC- CAA- CTG- CGA- GAC- GTT- AAA- CAT- ACA- CCA-
```

```
 20                                                    30
Asp  Arg  Gly  Phe  Tyr  Phe  Asn  Lys  Pro  Thr  Gly  Tyr  Gly  Ser
GAT- CGT- GGT- TTC- TAC- TTC- AAC- AAA- CCG- ACC- GGC- TAT- GGC- TCC-
CTA- GCA- CCA- AAG- ATG- AAG- TTG- TTT- GGC- TGG- CCG- ATA- CCG- AGG-
```

```
                        40
Ser  Ser  Arg  Arg  Ala  Pro  Gln  Thr  Gly  Ile  Val  Asp  Glu  Cys
AGC- TCT- CGT- CGC- GCA- CCG- CAG- ACT- GGT- ATC- GTA- GAC- GAA- TGC-
TCG- AGA- GCA- GCG- CGT- GGC- GTC- TGA- CCA- TAG- CAT- CTG- CTT- ACG-
```

```
           50                                           60
Cys  Phe  Arg  Ser  Cys  Asp  Leu  Arg  Arg  Leu  Glu  Met  Tyr  Cys
TGT- TTT- CCT- TCT- TGC- GAT- CTC- CGC- CGT- CTG- GAA- ATG- TAC- TGT-
ACA- AAA- GCA- AGA- ACG- CTA- GAG- GCG- GCA- GAC- CTT- TAC- ATG- ACA-
```

```
                             70
Ala  Pro  Leu  Lys  Pro  Ala  Lys  Ser  Ala  stop  stop  BamHI
GCT- CCA- CTG- AAG- CCA- GCA- AAA- TCC- GCG- TGA - TAG - 3'
CGA- GGT- GAC- TTC- GGT- CGT- TTT- AGG- CGC- ACT - ATC - CTAG- 5'
``` pCE-SMtrp pCE-SM31

Fra-B-1

Fra-B-3

EXPRESSION VECTOR FOR INSULIN-LIKE GROWTH FACTOR I AND METHOD OF PRODUCTION

This application is a continuation of application Ser. No. 07/488,459, filed Feb. 26, 1990, abandoned, which is a continuation of application Ser. No. 07/105,180, filed on Oct. 6, 1987, now abandoned.

This invention relates to a method for the preparation of insulin-like growth factor I (IGF-I). More particularly, it relates to a method for the preparation of methionyl insulin-like growth factor I (Met-IGF-I) using recombinant DNA technology, and vectors for use in the method.

Insulin-like growth factor (IGF) was separated, as an ethanol soluble fraction, from other insulin-like peptides occurring in blood. IGF includes insulin-like growth factor I (IGF-I) and insulin-like growth factor II (IGF-II). It is known that these two factors promote the growth of various tissue cells, and that their bio-synthesis and secretion are governed by growth hormones.

IGFs belong to a class of somatomedins which mediate the growth-promoting actions of growth hormones, and may be useful in the treatment of disorders such as dwarfism, osteoporosis, cartilage degeneration, heart and skeletal muscle deterioration, wound and carbohydrate dysfunction. IGF-I is known to be more closely related to growth hormones than IGF-II, and to be the same substance as somatomedin C.

Heretofore, IGF-I has been extracted from human serum in very low yields and with contaminants. Therefore, it would be a significant advance in the art if an efficient means for producing large quantities of pure IGF-I is developed.

Recently, it has become feasible to biosynthesize various biologically active substances in large scale owing to the development of the recombinant DNA technology. Attempts have also been made on the synthesis of IGF-I by such technology.

As is known in the art of recombinant technology, small peptides such as IGF-I (Mr=about 7,000-7,500) are extremely difficult to produce by direct expression because the expressed peptides are decomposed by the action of proteases in host cells. This problem may be overcomed to some extent by expressing the IGF-I in the form of a fused peptide with an appropriate additional peptide. The expressed fused peptide may be subsequently processed in vivo or in vitro to release IGF-I. For instance, Japanese Patent Publication (Kokai) No. 205997/1984 discloses the preparation of IGF-I using recombinant DNA technology. The expression system employed in the publication, which comprises replication origin, promoter, leader sequence, structural gene bearing processing signal, and termination signal, was constructed and transformed into yeast cells. The transformants were then incubated to express pre-IGF-I in the form of a fused peptide, which was then processed and secreted into the medium.

The inventors have also constructed an expression vector capable of expressing IGF-I in the form of a fused peptide in *Esherichia coli*. The host transformed with the vector was cultured, and the expressed fused peptide was processed by in vitro cleavage using cyanogen bromide or collagenase to obtain IGF-I (Japanese Patent Publication (Kokai) No. 1396/1986).

However, these known methods have a drawback that they require complicated procedures to cleave the fused peptide and separate IGF-I from other components. Therefore, an efficient method for overcoming such drawback has been waited for a long time.

The inventors have found that the cleavage of IGF-I due to the action of proteases occuring in host cells can be obviated when a certain kind of peptide is simultaneously expressed and retained in the host cells together with the desired peptide. This was established using two-cistron expression system in the recombinant DNA technology. This invention is based upon this finding and provides for two-cistronic vectors functional and replicatable in *E. coli*, which essentially contain DNA sequences encoding IGF-I and protective peptide which is capable of preventing the cellular proteases from decomposing IGF-I.

The invention also provides for the host cell transformed with the two-cistronic expression vector.

The invention further provides for a method for preparing IGF-I by culturing the transformant under appropriate conditions for the expression of IGF-I-encoding gene.

For the purpose of the invention, as disclosed and claimed herein, the following terms are defined below.

IGF-I gene - structural gene of IGF-I, or DNA sequence encoding IGF-I.

Met-IGF-I - a derivative of IGF-I, which has an additional methionyl residue at N-terminus of IGF-I.

$Amp^R$ - ampicillin-resistant phenotype or gene conferring the same.

$Tet^R$ - tetracycline-resistant phenotype or gene conferring the same.

$Amp^S$ - ampicillin-sensitive phenotype or gene conferring the same.

$Tet^S$ - tetracycline-sensitive phenotype or gene conferring the same.

Cistron - a functional gene unit which at least comprises translation initiating signal (start codon), structural gene encoding a peptide, and translation terminating signal (stop codon).

LH - left half of γ-interferon

RH - right half of γ-interferon

Cd - C-domain of IGF-I

α-hANP - α-human atrial natriuretic polypeptide

A polycistronic vector has been disclosed by B.E. Schnoer, Proc. Natl. Acad. Sci. USA, 81 5403-5407 (1984). The author constructed a vector having two cistrons, in which the coding region capable of enhancing the expression of bGH (bovin GH) was incorporated into the first cistron, and the coding region for Met-bGH was introduced into the second cistron. The first cistron encodes a polypeptide consisting of 20-25 amino acids, which is useful to prevent the formation of a stem and loop structure of mRNA and to enhance the binding of mRNA to the ribosome.

The two-cistronic expression vector of the present invention contains a DNA sequence encoding a relatively large "protective peptide" (i.e., Mr=about 500-50,000) in the first cistron and IGF-I gene in the second cistron. The protective peptide is specific in its ability to prevent the proteolytic cleavage of IGF-I. As IGF-I is a basic peptide which is usually labile to proteases, the protective peptide is preferably selected from acidic peptides which are capable of forming a complex with IGF-I. Since the molecular weight of IGF-I is reported to be about 7,000-7,500, it is preferable that the molecular weight of the protective peptide is between about 500–50,000, more preferably about 3,000–15,000, and that the isoelectric point (pI) of the peptide is between 4.0–7.0, more preferably 5.0–6.0. Illustrative protective peptides are peptide Cd (encoded by Fra-B-7 in FIG. 16), peptide LH (encoded by Fra-B-4 in FIG. 13) and Cd-LH fused peptide (encoded by Fra-B-6). In view of pI value, the Cd-LH is the most preferable peptide to use in the present expression vectors.

Illustrative expression vectors of the invention, pCE-SMtrp and pCE-SM3t (FIGS. 2.1 and 2.2, respectively), contain a DNA sequence encoding Cd-LH in the first cistron and a DNA sequence encoding IGF-I in the second cistron. These DNA sequences are transcribed, when the vector is incorporated in a suitable host, to polycistronic mRNAs which, in turn, are translated to give a couple of peptides. These two-cistronic vectors of the invention are schematically shown below:

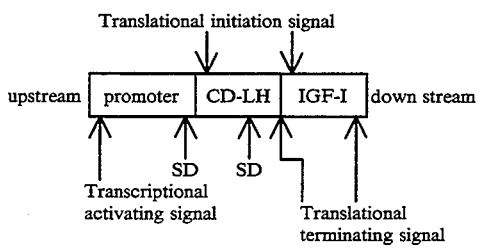

It can be seen from the above illustration that each peptide-encoding gene is preceded by a SD (Shine-Dalgarno) sequence which enhances the translation of the DNA sequence contained in each cistron. The expression vectors of the invention contain the first SD sequence located upstream from the translational initiation signal of the first cistron, and the second SD sequence located upstream from the translational terminating signal of the first cistron. Accordingly, the second SD sequence is a part of the nucleotide sequence encoding the protective peptide.

Therefore, this invention provides for a recombinant DNA expression vectors for the production in E. coli of Met-IGF-I efficiently, said vector comprises in series:

a) a promoter-encoding gene;

b) the first cistron comprising a gene encoding a protective peptide with a molecular weight of about 500–50,000, said gene containing a translational initiation signal immediately adjacent to the codon encoding the N-terminus of said peptide and a translational termination signal positioned downstream from the codon encoding the C-terminus of said peptide;

c) the second cistron comprising a gene encoding IGF-I, said gene containing a translational initiation signal immediately adjacent to the codon encoding the N-terminus of IGF-I and a translational termination signal downstream from the codon encoding the C-terminus of IGF-I; subject to the limitation that said vector contains two SD sequences each located upstream from the codon for the N-terminus of each peptide, and that said vector is selectable and autonomously replicatable in E. coli. The present vector gives Met-IGF-I upon expression, which is as much useful as native IGF-I for medical use.

The nucleotide sequence of the peculiar region where the tranlational termination signal of the first cistron and the translational initiation signal of the second cistron meet together can be more specifically described as shown below:

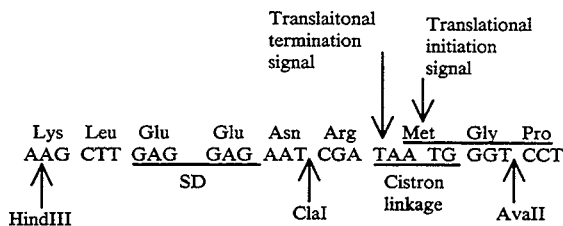

In the above, A is deoxyadenyl, G is deoxyguanyl, C is deoxycytidyl, and T is thymidyl.

As can be seen from the above schema, the "ATG" codon which encodes methionine adjacent to the N-terminus of IGF-I is overlapped with the "TAA" translational termination signal which locates at the 3' terminus of the nucleotide sequence of the protective peptide. Nucleotide sequences positioned in the region where the translational termination signal of the first cistron and the translational initiation signal of the second cistron meet together is not limited to the above particular sequence, and other sequences are available, such as TGATG, or ATGA in which the order of the termination codon and the initiation codon is reversed, or TAGATG, TAAATG or TGAATG in which the termination codon and initiation codon are located in alignment. As shown in the above schema, the SD sequence for the second cistron may be a part of the nucleotide sequence encoding a protective peptide. In such a case, the SD sequence is preferably positioned 5–15 bp, preferably 6–8 bp upstream from the coding region of translational termination and initiation signals. This can be accomplished using appropriately constructed DNA linkers, such as Fra-A-3, described hereinafter.

This DNA linker, Fra-A-3, was ligated to the 5' terminus of the IGF-I gene to obtain a DNA fragment (Fra-A-7), which was then ligated into the 4.5 kbp HindIII-BamHI restriction fragment of α-hANP expression vector pCLaHtrpSd (Japanese Patent Publication (Kokai) No. 141900/1986) to form two-cistronic plasmid pCE-SMtrp. Alternatively, the Fra-A-7 was ligated into the 4137 bp HindIII-BamHI restriction fragment of plasmid pCLaHtrp3t (prepared in Preparation 11) to form two-cistronic plasmid pCE-SM3t. When one of these plasmids is transformed into host cells, the resultant transformants produce both peptides simultaneously. This results in safe maintenance of intact Met-IGF-I peptide within the host cells owing to the complex formation between the basic peptide, Met-IGF-I, and the acidic peptide, Cd-LH. Thus, the complex shows resistance to cellular proteases. The isolation of Met-IGF-I from the transformants can be easily performed using conventional methods. For example, after the cultured cells are harvested and lyzed, the lysates are subjected to an appropriate process suitable for the separation of Met-IGF-I from Cd-LH on the basis of the difference in physical properties, such as solubility in acidic solvent.

For convenience of expression of Met-IGF-I in E. coli, plasmid pBR322 was used as a starting material for the construction of two-cistronic vectors of the invention. However, as those skilled in the art will recognize, many other plasmids, such as pUC9 or pAT153, can be used in stead of pBR322 so long as they are capable of replicating in E. coli. Bacteriophages can also be used for the construction of the vectors of the invention.

The construction of the vectors of the invention does not require the use of any specific promoter, and it can be selected from those commonly used. The illustrative vectors of the invention comprise one or more artificial promoters which were synthesized based on the nucleotide sequence of the native promoter of tryptophan operon. For the purpose of the invention, three artificial trp promoters were synthesized. The transcription activating sequences of these three synthetic promoters were same and identical, but the sequence of the 3' terminal region differed from each other. These were designated "trp promoter I", "trp promoter II" and "trp promoter III".

Transcription termination sequence may be derived from the starting material, i.e., phages or plasmids used for the construction of the present vectors. Alternatively, a synthesized sequence, for example, synthesized fd phage terminator may be used as illustrated in working examples.

For the convenience of the description, the term "synthesized" or "artificial" will be omitted hereinafter in connection with DNA fragments that code for peptides, trp promoters, or fd phage terminator.

DETAILED DESCRIPTION OF THE INVENTION

The starting plasmid pBR322 containing $Tet^R$ and $Amp^R$ was digested with restriction enzymes EcoRI and BamHI and the resultant large DNA restriction fragment was isolated, which was then ligated to trp promoter II (Fra-B-1, 163 bp) to form plasmid pTrpEB7 which lacks for $Tet^R$. Plasmid pTrpEB7 was digested with restriction enzymes EcoRI and BamHI, and the resultant large fragment containing the trp promoter I, which comprises nucleotide sequence corresponding to the sequence positioned upstream from EcoRI site of Trp promoter II, was obtained. To the DNA fragment was inserted the small EcoRI-BamHI restriction fragment of plasmid pBR322 to form plasmid pBR322trp comprising trp promoter I, $Tet^R$ and $Amp^R$. Trp promoter III (Fra-B-3) was ligated into the EcoRI - ClaI restriction fragment of plasmid pBR322trp to form plasmid pBR322dtrpS.

The nucleotide sequence of trp promoters II and III (Fra-B-1 and Fra-B-3) are as follows.

Fra-B-1 (163 bp) Synthetic promotor II gene

EcoRI*
AATTTGCCGACATCATAACGGTTCTGGCAAATATTCTGAAATGAGC—
    ACGGCTGTAGTATTGCCAAGACCGTTTATAAGACTTTACTCG—

HpaI
TGTTGACAATTAATCATCGAACTAGTTAACTAGTACGCAAGTTCACGTAAA—
ACAACTGTTAATTAGTAGCTTGATCAATTGATCATGCGTTCAAGTGCATTT—

EcoRI
AAGGGTATCGAATTCATGGCTGGTTGTAAGAACTTCTTTTGGAAGACTTTC—
TTCCCATAGCTTAAGTACCGACCAACATTCTTGAAGAAAACCTTCTGAAAG—

BamHI
ACTTCGTGTTGATAG
TGAAGCACAACTATCCTAG

Fra-B-3 (105 bp) Synthetic trp promotor III gene

EcoRI*
AATTTGCCGACATCATAACGGTTCTGGCAAATATTCTGAAATGAGCTGTTGA—
    ACGGCTGTAGTATTGCCAAGACCGTTTATAAGACTTTACTCGACAACT—

HpaI                                         ClaI
CAATTAATCATCGAACTAGTTAACTAGTACGCAAGTTCACGTAAAAGGGTAT
GTTAATTAGTAGCTTGATCAATTGATCATGCGTTCAAGTGCATTTTTCCCATAGC

A schematic illustration of the construction protocol for each of the intermediate plasmid pTrpEB7 and plasmid pBR322dtrpS encoding trp promoter I and III is presented respectively in FIG. 3 and 4 of the accompanying drawings.

Plasmid pCdγ which codes for a fused peptide of Cd and LH-RH was constructed as follows.

LH-encoding gene (Fra-B-4) was ligated into the EcoRI-BamHI restriction fragment of plasmid pBR322 to form plasmid pLH107. Plasmid pLH107 was digested with restriction enzymes HindIII and BamHI to delete the nucleotide sequence of Fra-B-4 located downstream from the HindIII site. RH gene (Fra-B-5) was then ligated into the resulting DNA fragment to form plasmid pγF-3, from which EcoRI-BamHI restriction fragment, i.e. LH-RH-encoding gene (Fra-B-6), was isolated.

The LH-RH-encoding gene (Fra-B-6) was ligated into the EcoRI-BamHI restriction fragment of plasmid pTrpEB7 to form plasmid pγtrp which contains the LH-RH-encoding gene located downstream from the trp promoter I. The large HpaI-EcoRI restriction fragment of plasmid pγtrp was ligated to a DNA fragment containing part of trp promoter III and Cd-encoding gene (Fra-B-7) to form plasmid pCd γ which comprises trp promoter I and trp promoter III and Cd- and LH-RH- encoding genes in this order. The nucleotide and amino acids sequences of Fra-B-4, Fra-B-5, Fra-B-6, and Fra-B-7 are shown bellow. The illustrative construction protocol of plasmid pCdγ is presented in FIG. 5.

Fra-B-4 (236 bp) LH gene

```
                          EcoRI        1
                                   Met Cys Tyr Cys Gln Asp Pro Tyr
                          AATTC—ATG—TGT—TAC—TGC—CAG—GAC—CCA—TAT—
                              G—TAC—ACA—ATG—ACG—GTC—CTG—GGT—ATA—

10
Val Lys Glu Ala Glu Asn Leu Lys Lys Tyr Phe Asn Ala Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His Ser Asp Val Ala Asp Asn Gly Thr Leu Phe Leu Gly Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu Lys Asn Trp Lys Glu Glu Ser Asp Arg Lys Ile Met Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                 HindIII     60
Ser Gln Ile Val Ser Phe Tyr Phe Lys Leu Phe Lys Asn Phe
AGC—CAA—ATT—GTC—TCC—TTT—TAC—TTC—AAG—CTT—TTC—AAA—AAC—TTT—
TCG—GTT—TAA—CAG—AGG—AAA—ATG—AAG—TTC—GAA—AAG—TTT—TTG—AAA—

70                  stop stop stop BamHI
Lys Asp Asp Gln Ser Ile Gln Lys Ser Val
AAG—GAT—GAC—CAG—AGC—ATC—CAA—AAG—AGT—GTG—TAA—TGA—TAG
TTC—CTA—CTG—GTC—TCG—TAG—GTT—TTC—TCA—CAC—ATT—ACT—ATCCTAG Fra-B-5 (270 bp) RH gene HindIII      60
                                                    Phe Lys
                                              AG—CTT—TTC—AAA—
                                               A—AAG—TTT—

70
Asn Phe Lys Asp Asp Gln Ser Ile Gln Lys Ser Val Glu Thr
AAC—TTT—AAG—GAT—GAC—CAG—AGC—ATC—CAA—AAG—AGT—GTG—GAG—ACC—
TTG—AAA—TTC—CTA—CTG—GTC—TCG—TAG—GTT—TTC—TCA—CAC—CTC—TGG—

80
Ile Lys Glu Asp Met Asn Val Lys Phe Phe Asn Ser Asn Lys
ATC—AAG—GAA—GAC—ATG—AAT—GTC—AAG—TTT—TTC—AAT—AGC—AAC—AAA—
TAG—TTC—CTT—CTG—TAC—TTA—CAG—TTC—AAA—AAG—TTA—TCG—TTG—TTT—

90                                    100
Lys Lys Arg Asp Asp Phe Glu Lys Leu Thr Asn Tyr Ser Val
AAG—AAA—CGT—GAT—GAC—TTC—GAA—AAG—CTG—ACT—AAT—TAT—TCG—GTA—
TTC—TTT—GCA—CTA—CTG—AAG—CTT—TTC—GAC—TGA—TTA—ATA—AGC—CAT—

110
Thr Asp Leu Asn Val Gln Arg Lys Ala Ile His Glu Leu Ile
ACT—GAC—TTG—AAT—GTC—CAA—CGC—AAA—GCA—ATA—CAT—GAA—CTC—ATC—
TGA—CTG—AAC—TTA—CAG—GTT—GCG—TTT—CGT—TAT—GTA—CTT—GAG—TAG—

120                                             130
Gln Val Met Ala Glu Leu Ser Pro Ala Ala Lys Thr Gly Lys
CAA—GTG—ATG—GCT—GAA—CTG—TCG—CCA—GCA—GCT—AAA—ACA—GGG—AAG—
GTT—CAC—TAC—CGA—CTT—GAC—AGC—GGT—CGT—CGA—TTT—TGT—CCC—TTC—

140
Arg Lys Arg Ser Gln Met Leu Phe Gln Gly Arg Arg Ala Ser
CGA—AAA—CGT—AGT—CAG—ATG—CTG—TTT—CAA—GGT—CGA—AGA—GCA—TCC—
GCT—TTT—GCA—TCA—GTC—TAC—GAC—AAA—GTT—CCA—GCT—TCT—CGT—AGG— stop BamHI
Gln
CAG—TAA—G
GTC—ATT—CCTAG

Fra-B-6 (450 bp) LH—RH gene

EcoRI        1
                                   Met Cys Tyr Cys Gln Asp Pro Tyr
                          AATTC—ATG—TGT—TAC—TGC—CAG—GAC—CCA—TAT—
                              G—TAC—ACA—ATG—ACG—GTC—CTG—GGT—ATA—
```

```
                    10                                          20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                HindIII       60
Ser  Gln  Ile  Val  Ser  Phe  Tyr  Phe  Lys  Leu  Phe  Lys
AGC—CAA—ATT—GTC—TCC—TTT—TAC—TTC—AAG—CTT—TTC—AAA—
TCG—GTT—TAA—CAG—AGG—AAA—ATG—AAG—TTC—GAA—AAG—TTT—

70
Asn  Phe  Lys  Asp  Asp  Gln  Ser  Ile  Gln  Lys  Ser  Val  GLu  Thr
AAC—TTT—AAG—GAT—GAC—CAG—AGC—ATC—CAA—AAG—AGT—GTG—GAG—ACC—
TTG—AAA—TTC—CTA—CTG—GTC—TCG—TAG—GTT—TTC—TCA—CAC—CTC—TGG—

80
Ile  Lys  Glu  Asp  Met  Asn  Val  Lys  Phe  Phe  Asn  Ser  Asn  Lys
ATC—AAG—GAA—GAC—ATG—AAT—GTC—AAG—TTT—TTC—AAT—AGC—AAC—AAA—
TAG—TTC—CTT—CTG—TAC—TTA—CAG—TTC—AAA—AAG—TTA—TCG—TTG—TTT—

90                                      100
Lys  Lys  Arg  Asp  Asp  Phe  Glu  Lys  Leu  Thr  Asn  Tyr  Ser  Val
AAG—AAA—CGT—GAT—GAC—TTC—GAA—AAG—CTG—ACT—AAT—TAT—TCG—GTA—
TTC—TTT—GCA—CTA—CTG—AAG—CTT—TTC—GAC—TGA—TTA—ATA—AGC—CAT—

110
Thr  Asp  Leu  Asn  Val  Gln  Arg  Lys  Ala  Ile  His  Glu  Leu  Ile
ACT—GAC—TTG—AAT—GTC—CAA—CGC—AAA—GCA—ATA—CAT—GAA—CTC—ATC—
TGA—CTG—AAC—TTA—CAG—GTT—GCG—TTT—CGT—TAT—GTA—CTT—GAG—TAG—

120                                          130
Gln  Val  Met  Ala  Glu  Leu  Ser  Pro  Ala  Ala  Lys  Thr  Gly  Lys
CAA—GTG—ATG—GCT—GAA—CTG—TCG—CCA—GCA—GCT—AAA—ACA—GGG—AAG—
GTT—CAC—TAC—CGA—CTT—GAC—AGC—GGT—CGT—CGA—TTT—TGT—CCC—TTC—

140
Arg  Lys  Arg  Ser  Gln  Met  Leu  Phe  Gln  Gly  Arg  Arg  Ala  Ser
CGA—AAA—CGT—AGT—CAG—ATG—CTG—TTT—CAA—GGT—CGA—AGA—GCA—TCC—
GCT—TTT—GCA—TCA—GTC—TAC—GAC—AAA—GTT—CCA—GCT—TCT—CGT—AGG— stop  BamHI
Gln
CAG—TAA—G
GTC—ATT—CCTAG
```

Fra-B-7 (124 bp) Peptide Cd gene with a part of DNA fragment of synthetic trp promoter III gene

```
HpaI                              ClaI          Met  Phe  Tyr  Phe
  AACTAGTACGCAAGTTCACGTAAAAAGGGTATCGATAAA—ATG—TTC—TAC—TTC—
  TTGATCATGCGTTCAAGTGCATTTTTCCCATAGCTATTT—TAC—AAG—ATG—AAG—

Asn  Lys  Pro  Thr  Gly  Tyr  Gly  Ser  Ser  Ser  Arg  Arg  Ala  Pro  Gln
AAC—AAA—CCG—ACC—GGC—TAT—GGC—TCC—AGC—TCT—CGT—CGC—GCA—CCG—CAG—
TTG—TTT—GGC—TGG—CCG—ATA—CCG—AGG—TCG—AGA—GCA—GCG—CGT—GGC—GTC—

EcoRI
Thr  Gly  Ile  Val  Asp  Glu  Gly  Gly  Asp  Glu  Phe
ACT—GGT—ATC—GTA—GAC—GAG—GGT—GGC—GAT—G
TGA—CCA—TAG—CAT—CTG—CTC—CCA—CCG—CTA—CTT—AA
```

Plasmid pCLaHtrpSd which encodes a fused protein of Cd-LH and α-hANP was constructed as follows.

The ClaI-BamHI restriction fragment of plasmid pCdγ (Fra-B-8) was inserted into the ClaI-BamHI restriction site of plasmid p322dtrpS to form a expression plasmid pCdγtrpSd for a fused peptide of Cd and LH-RH.

The α-hANP-encoding DNA with linker DNA (Fra-B-9) was ligated into HindIII-BamHI restriction fragment of plasmid pCdγtrpSd to form an expression vector pCLaHtrpSd encoding Cd-LH-α-hANP fused peptide. Fra-B-8 and Fra-B-9 are shown below. The illustrative construction protocol of plasmids pCdγtrpSd and pCLaHtrpSd are presented in FIG. 6.

Fra-B-8 (542 bp) Cd—LH—RH gene

```
        ClaI         Met  Phe  Tyr  Phe  Asn  Lys  Pro  Thr
    CGATAAA—ATG—TTC—TAC—TTC—AAC—AAA—CCG—ACC—
        TATTT—TAC—AAG—ATG—AAG—TTG—TTT—GGC—TGG—

Gly  Tyr  Gly  Ser  Ser  Ser  Arg  Arg  Ala  Pro  Gln  Thr  Gly  Ile  Val
GGC—TAT—GGC—TCC—AGC—TCT—CGT—CGC—GCA—CCG—CAG—ACT—GGT—ATC—GTA—
CCG—ATA—CCG—AGG—TCG—AGA—GCA—GCG—CGT—GGC—GTC—TGA—CCA—TAG—CAT;—

EcoRI
Asp  Glu  Gly  Gly  Asp  Glu  Phe  Met  Cys  Tyr  Cys  Gln  Asp  Pro  Tyr
GAC—GAG—GGT—GGC—GAT—GAA—TTC—ATG—TGT—TAC—TGC—CAG—GAC—CCA—TAT—
CTG—CTC—CCA—CCG—CTA—CTT—AAG—TAC—ACA—ATG—ACG—GTC—CTG—GGT—ATA—

10                                                    20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                         HindIII    60
Ser  Gln  Ile  Val  Ser  Phe  Tyr  Phe  Lys  Leu  Phe  Lys
AGC—CAA—ATT—GTC—TCC—TTT—TAC—TTC—AAG—CTT—TTC—AAA—
TCG—GTT—TAA—CAG—AGG—AAA—ATG—AAG—TTC—GAA—AAG—TTT—

70
Asn  Phe  Lys  Asp  Asp  Gln  Ser  Ile  Gln  Lys  Ser  Val  Glu  Thr
AAC—TTT—AAG—GAT—GAC—CAG—AGC—ATC—CAA—AAG—AGT—GTG—GAG—ACC—
TTG—AAA—TTC—CTA—CTG—GTC—TCG—TAG—GTT—TTC—TCA—CAC—CTC—TGG—

80
Ile  Lys  Glu  Asp  Met  Asn  Val  Lys  Phe  Phe  Asn  Ser  Asn  Lys
ATC—AAG—GAA—GAC—ATG—AAT—GTC—AAG—TTT—TTC—ATT—AGC—AAC—AAA—
TAG—TTC—CTT—CTG—TAC—TTA—CAG—TTC—AAA—AAG—TTA—TCG—TTG—TTT—

90                                                100
Lys  Lys  Arg  Asp  Asp  Phe  Glu  Lys  Leu  Thr  Asn  Tyr  Ser  Val
AAG—AAA—CGT—GAT—GAC—TTC—GAA—AAG—CTG—ACT—AAT—TAT—TCG—GTA—
TTC—TTT—GCA—CTA—CTG—AAG—CTT—TTC—GAC—TGA—TTA—ATA—AGC—CAT—

110
Thr  Asp  Leu  Asn  Val  Gln  Arg  Lys  Ala  Ile  His  Glu  Leu  Ile
ACT—GAC—TTG—AAT—GTC—CAA—CGC—AAA—GCA—ATA—CAT—GAA—CTC—ATC—
TGA—CTG—AAC—TTA—CAG—GTT—GCG—TTT—CGT—TAT—GTA—CTT—GAG—TAG—

120                                            130
Gln  Val  Met  Ala  Glu  Leu  Ser  Pro  Ala  Ala  Lys  Thr  Gly  Lys
CAA—GTG—ATG—GCT—GAA—CTG—TCG—CCA—GCA—GCT—AAA—ACA—GGG—AAG—
GTT—CAC—TAC—CGA—CTT—GAC—AGC—GGT—CGT—CGA—TTT—TGT—CCC—TTC—

140
Arg  Lys  Arg  Ser  Gln  Met  Leu  Phe  Gln  Gly  Arg  Arg  Ala  Ser
CGA—AAA—CGT—AGT—CAG—ATG—CTG—TTT—CAA—GGT—CGA—AGA—GCA—TCC—
GCT—TTT—GCA—TCA—GTC—TAC—GAC—AAA—GTT—CCA—GCT—TCT—CGT—AGG— stop BamHI
Gln
CAG—TAA—G
GTC—ATT—CCTAG
```

Fra-B-9 (134 bp) α-hANP gene with linker DNA

```
HindIII
Lys  Leu  Glu  Val  Glu  His  Glu  Phe  Gly  Met  Gly  Gly  Glu  Ala  Lys
  AG—CTT—GAA—GTT—GAG—CAT—GAA—TTC—GGT—ATG—GGC—GGT—GAA—GCT—AAA—
      A—CTT—CAA—CTC—GTA—CTT—AAG—CCA—TAC—CCG—CCA—CTT—CGA—TTT—

Ser  Leu  Arg  Arg  Ser  Ser  Cys  Phe  Gly  Gly  Arg  Met  Asp  Arg  Ile
TCT—CTG—CGT—AGA—TCC—TCT—TGC—TTT—GGT—GGC—CGT—ATG—GAC—CGC—ATC—
AGA—GAC—GCA—TCT—AGG—AGA—ACG—AAA—CCA—CCG—GCA—TAC—CTG—GCG—TAG—
```

```
                                                              stop  stop
                                                                         BamHI
Gly   Ala   Gln   Ser   Gly   Leu   Gly   Cys   Asn   Ser   Phe   Arg   Tyr
GGT—GCT—CAG—TCC—GGT—CTG—GGC—TGT—AAC—TCT—TTC—CGT—TAC—TGA—TAG
CCA—CGA—GTC—AGG—CCA—GAC—CAG—ACA—TTG—AGA—AAG—GCA—ATG—ACT—ATC—CTAG.
```

The DNA fragment (Fra-A-7) useful in the construction of the present two-cistronic IGF-I expression vectors was prepared as follows.

Fra-B-4 was ligated into the large EcoRI-BamHI restriction fragment of plasmid pTrpEB7 to form plasmid pLHtrp encoding trp promoter I and LH. IGF-I-encoding gene was prepared for the construction of the present vectors in the following manner. Plasmid pBR322 was digested with restriction enzymes EcoRI and BamHI and the large restriction fragment was isolated, to which was then ligated the IGF-I encoding DNA (Fra-B-10) to form plasmid pSdm1. From the plasmid pSdm1, EcoRI-BamHI restriction fragment encoding IGF-I was isolated and to which fragment was ligated oligonucleotides m1 and m2 to form Fra-B-11. Fra-B-11 was ligated into the HindIII-BamHI restriction fragment of plasmid pLHtrp to form plasmid pLHSdMmtrp. The nucleotide and amino acids sequences of Fra-B-10 and Fra-B-11 are shown below. The illustrative construction protocol of plasmid pLHSdMmtrp is presented in FIG. 7.

Fra-B-10  (224 bp) IGF-I gene

```
          EcoRI                    AvaII
                Met   Gly   Pro   Glu   Thr   Leu   Cys   Gly
          AATTC—ATG—GGT—CCT—GAA—ACT—CTG—TGC—GGC—
              G—TAC—CCA—GGA—CTT—TGA—GAC—ACG—CCG—

10                                                       20
Ala   Glu   Leu   Val   Asp   Ala   Leu   Gln   Phe   Val   Cys   Gly   Asp   Arg
GCT—GAA—CTG—GTT—GAC—GCT—CTG—CAA—TTT—GTA—TGT—GGT—GAT—CGT—
CGA—CTT—GAC—CAA—CTG—CGA—GAC—GTT—AAA—CAT—ACA—CCA—CTA—GCA—

30
Gly   Phe   Tyr   Phe   Asn   Lys   Pro   Thr   Gly   Tyr   Gly   Ser   Ser   Ser
GGT—TTC—TAC—TTC—AAC—AAA—CCG—ACC—GGC—TAT—GGC—TCC—AGC—TCT—
CCA—AAG—ATG—AAG—TTG—TTT—GGC—TGG—CCG—ATA—CCG—AGG—TCG—AGA—

40
Arg   Arg   Ala   Pro   Gln   Thr   Gly   Ile   Val   Asp   Glu   Cys   Cys   Phe
CGT—CGC—GCA—CCG—CAG—ACT—GGT—ATC—GTA—GAC—GAA—TGC—TGT—TTT—
GCA—GCG—CGT—GGC—GTC—TGA—CCA—TAG—CAT—CTG—CTT—ACG—ACA—AAA—

50                                                       60
Arg   Ser   Cys   Asp   Leu   Arg   Arg   Leu   Glu   Met   Tyr   Cys   Ala   Pro
CGT—TCT—TGC—GAT—CTC—CGC—CGT—CTG—GAA—ATG—TAC—TGT—GCT—CCA—
GCA—AGA—ACG—CTA—GAG—GCG—GCA—GAC—CTT—TAC—ATG—ACA—CGA—GGT—

70 stop stop BamHI
Leu   Lys   Pro   Ala   Lys   Ser   Ala
CTG—AAG—CCA—GCA—AAA—TCC—GCG—TGA—TAG-3'
GAC—TTC—GGT—CGT—TTT—AGG—CGC—ACT—ATC—CTAG-5'
```

Fra-B-11  (242 bp) IGF-I gene with linker DNA, same to
Fra-A-4

```
HindIII                           EcoRI              AvaII
     Leu   Glu   Val   Lys   His   Glu   Phe   Met   Gly   Pro   Glu   Thr   Leu
   AG—CTT—GAA—GTA—AAA—CAT—GAA—TTC—ATG—GGT—CCT—GAA—ACT—CTG—
       A—CTT—CAT—TTT—GTA—CTT—AAG—TAC—CCA—GGA—CTT—TGA—GAC—

10
Cys   Gly   Ala   Glu   Leu   Val   Asp   Ala   Leu   Gln   Phe   Val   Cys   Gly
TGC—GGC—GCT—GAA—CTG—GTT—GAC—GCT—CTG—CAA—TTT—GTA—TGT—GGT—
ACG—CCG—CGA—CTT—GAC—CAA—CTG—CGA—GAC—GTT—AAA—CAT—ACA—CCA—

20                                           30
Asp   Arg   Gly   Phe   Tyr   Phe   Asn   Lys   Pro   Thr   Gly   Tyr   Gly   Ser
GAT—CGT—GGT—TTC—TAC—TTC—AAC—AAA—CCG—ACC—GGC—TAT—GGC—TCC—
CTA—GCA—CCA—AAG—ATG—AAG—TTG—TTT—GGC—TGG—CCG—ATA—CCG—AGG—

40
Ser   Ser   Arg   Arg   Ala   Pro   Gln   Thr   Gly   Ile   Val   Asp   Glu   Cys
AGC—TCT—CGT—CGC—GCA—CCG—CAG—ACT—GGT—ATC—GTA—GAC—GAA—TGC—
TCG—AGA—GCA—GCG—CGT—GGC—GTC—TGA—CCA—TAG—CAT—CTG—CTT—ACG—

50                                                       60
Cys   Phe   Arg   Ser   Cys   Asp   Leu   Arg   Arg   Leu   Glu   Met   Tyr   Cys
TGT—TTT—CGT—TCT—TGC—GAT—CTC—CGC—CGT—CTG—GAA—ATG—TAC—TGT—
ACA—AAA—GCA—AGA—ACG—CTA—GAG—GCG—GCA—GAC—CTT—TAC—ATG—ACA—
```

```
                                             70  stop stop BamHI
Ala  Pro  Leu  Lys  Pro  Ala  Lys  Ser  Ala
GCT—CCA—CTG—AAG—CCA—GCA—AAA—TCC—GCG—TGA—TAG-3'
CGA—GGT—GAC—TTC—GGT—CGT—TTT—AGG—CGC—ACT—ATC—CTAG-5'
```

Plasmid pLHSdMmtrp was digested with restriction enzymes HindIII and BamHI to obtain Fra-A-4 (same as Fra-B-11) containing a gene encoding IGF-I with linker DNA. The fragment was digested with AvaII to give Fra-A-5 containing a translational termination codon at 3' terminus.

Fra-A-3 which comprises SD sequence and termination codon was constructed by ligating the ClaI restriction fragment of Fra-A-1 (i.e., Fra-A-2) to oligonucleotides CT5 and CT6. Fra-A-3 was ligated to Fra-A-5 at the AvaII restriction site to form Fra-A-6 which contained SD sequence, translational termination signal, translational initiation signal and IGF-I-encoding gene in series. Fra-A-6 was digested with HindIII restriction enzyme to obtain Fra-A-7. The nucleotide and amino acid sequences and the restriction sites of Fra-A-1, Fra-A-2, Fra-A-3, Fra-A-4, Fra-A-5, Fra-A-6 and Fra-A-7 are shown below. The illustrative synthesis protocol of Fra-A-7 is represented in FIG. 8.

Fra-A-1 (46 bp) Linker DNA containing internal SD sequence

```
                                             HindIII                              ClaI stop
Arg  Cys  Gln  Tyr  Arg  Asp  Leu  Lys  Leu  Glu  Glu  Asn  Arg        Met
 GT—TGC—CAG—TAC—CGC—GAC—CTG—AAG—CTT—GAG—GAG—AAT—CGA—TA—ATG—
    C—ATG—GCG—CTG—GAC—TTC—GAA—CTC—CTC—TTA—GCT—AT—TAC—

Ser  Leu  Arg
TCT
AGA—GAC—GC
```

Fra-A-2 (35 bp) Linker DNA containing internal SD sequence

```
                                             HindIII                              ClaI
Arg  Cys  Gln  Tyr  Arg  Asp  Leu  Lys  Leu  Glu  Glu  Asn
 GT—TGC—CAG—TAC—CGC—GAC—CTG—AAG—CTT—GAG—GAG—AAT
    C—ATG—GCG—CTG—GAC—TTC—GAA—CTC—CTC—TTA—GC
```

Fra-A-3 (44 bp) Linker DNA containing internal SD sequence

```
                                             HindIII                              ClaI stop        AvaII
Arg  Cys  Gln  Tyr  Arg  Asp  Leu  Lys  Leu  Glu  Glu  Asn  Arg        Met  Gly
 GT—TGC—CAG—TAC—CGC—GAC—CTG—AAG—CTT—GAG—GAG—AAT—CGA—TA—ATG—G
    C—ATG—GCG—CTG—GAC—TTC—GAA—CTC—CTC—TTA—GCT—AT—TAC—CCA—G
```

Fra-A-4 (242 bp) IGF-I gene with linker DNA, same to
  Fra-B-11

```
                       HindIII
                       Leu  Glu  Val  Lys  His—
                     AG—CTT—GAA—GTA—AAA—CAT—
                        A—CTT—CAT—TTT—GTA—

AvaII
Glu  Phe  Met  Gly  Pro  Glu  Thr  Leu  Cys  Gly  Ala  Glu  Leu  Val
GAA—TTC—ATG—GGT—CCT—GAA—ACT—CTG—TGC—GGC—GCT—GAA—CTG—GTT—
CTT—AAG—TAC—CCA—GGA—CTT—TGA—GAC—ACG—CCG—CGA—CTT—GAC—CAA—

Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT— stop BamHI
Lys  Ser  Ala
AAA—TCC—GCG—TGA—TAG
TTT—AGG—CGC—ACT—ATC—CTAG
```

Fra-A-5 (215 bp)

-continued

```
            AvaII
            Pro   Glu   Thr   Leu   Cys   Gly   Ala   Glu   Leu   Val
         GT—CCT—GAA—ACT—CTG—TGC—GGC—GCT—GAA—CTG—GTT—
            GA—CTT—TGA—GAC—ACG—CCG—CGA—CTT—GAC—CAA—

Asp   Ala   Leu   Gln   Phe   Val   Cys   Gly   Asp   Arg   Gly   Phe   Tyr   Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

Asn   Lys   Pro   Thr   Gly   Tyr   Gly   Ser   Ser   Ser   Arg   Arg   Ala   Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

Gln   Thr   Gly   Ile   Val   Asp   Glu   Cys   Cys   Phe   Arg   Ser   Cys   Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

Leu   Arg   Arg   Leu   Glu   Met   Tyr   Cys   Ala   Pro   Leu   Lys   Pro   Ala
CTC—CGC—CGT—CTG—GAA—ATG—TAC—TGT—TCT—CCA—CTG—AAG—CCA—GCA—
GAG—GCG—GCA—GAC—CTT—TAC—ATG—ACA—CGA—GGT—GAC—TTC—GTT—CGT— stop  BamHI
Lys   Ser   Ala
AAA—TCC—GCG—TGA—TAG
TTT—AGG—CGC—ACT—ATC—CTAG
```

Fra-A-6 (259 bp)

```
                              HindIII                        ClaI  stop
Arg   Cys   Gln   Tyr   Arg   Asp   Leu   Lys   Leu   Glu   Glu   Asn   Arg
   GT—TGC—CAG—TAC—CGC—GAC—CTG—AAG—CTT—GAG—GAG—AAT—CGA—TA—
      C—ATG—GCG—CTG—GAC—TTC—GAA—CTC—CTC—TTA—GCT—AT—

AvaII
Met   Gly   Pro   Glu   Thr   Leu   Cys   Gly   Ala   Glu   Leu   Val
ATG—GGT—CCT—GAA—ACT—CTG—TGC—GGC—GCT—GAA—CTG—GTT—
TAC—CCA—GGA—CTT—TGA—GAC—ACG—CCG—CGA—CTT—GAC—CAA—

Asp   Ala   Leu   Gln   Phe   Val   Cys   Gly   Asp   Arg   Gly   Phe   Tyr   Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

Asn   Lys   Pro   Thr   Gly   Tyr   Gly   Ser   Ser   Ser   Arg   Arg   Ala   Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

Gln   Thr   Gly   Ile   Val   Asp   Glu   Cys   Cys   Phe   Arg   Ser   Cys   Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

Leu   Arg   Arg   Leu   Glu   Met   Tyr   Cys   Ala   Pro   Leu   Lys   Pro   Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT— stop  stop  BamHI
Lys   Ser   Ala
AAA—TCC—GCG—TGA—TAG
TTT—AGG—CGC—ACT—ATC—CTAG
```

Fra-A-7 (238 bp)

```
                              HindIII                        ClaI  stop
                        Leu   Glu   Glu   Asn   Arg
                     AG—CTT—GAG—GAG—AAT—CGA—TA—
                        A—CTC—CTC—TTA—GCT—AT—

AvaII
Met   Gly   Pro   Glu   Thr   Leu   Cys   Gly   Ala   Glu   Leu   Val
ATG—GGT—CCT—GAA—ACT—CTG—TGC—GGC—GCT—GAA—CTG—GTT—
TAC—CCA—GGA—CTT—TGA—GAC—ACG—CCG—CGA—CTT—GAC—CAA—

Asp   Ala   Leu   Gln   Phe   Val   Cys   Gly   Asp   Arg   Gly   Phe   Tyr   Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

Asn   Lys   Pro   Thr   Gly   Tyr   Gly   Ser   Ser   Ser   Arg   Arg   Ala   Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

Gln   Thr   Gly   Ile   Val   Asp   Glu   Cys   Cys   Phe   Arg   Ser   Cys   Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—
```

```
Leu  Arg  Arg  Leu  Glu  Met  Tyr  Cys  Ala  Pro  Leu  Lys  Pro  Ala
CTC—CGC—CGT—CTG—GAA—ATG—TAC—TGT—GCT—CCA—CTG—AAG—CCA—GCA—
GAG—GCG—GCA—GAC—CTT—TAC—ATG—ACA—CGA—GGT—GAC—TTC—GGT—CGT— stop stop BamHI
Lys  Ser  Ala
AAA—TCC—GCG—TGA—TAG
TTT—AGG—CGC—ACT—ATC—CTAG
```

Fra-A-7 was then ligated into the HindIII-BamHI restriction fragment of α-hANP expression vector pCLaHtrpSd to replace the α-hANP-encoding gene with IGF-I-encoding gene to form the plasmid of the invention, pCE-SMtrp. The illustrative construction protocol is presented in FIG. 9.

Another IGF-I expression vector pCE-SM3t was constructed as follows.

The DNA sequence encoding Trp promoter III (Fra-B-3) was ligated into the EcoRI-ClaI restriction fragment of plasmid pBR322 to obtain plasmid pBR322trpSs containing Amp$^R$ and Tet$^R$. The ClaI-BamHI restriction fragment of plasmid pCLaHtrpSd (Fra-C-2 encoding Cd-LH and α-hANP) was ligated into the large ClaI-BamHI restriction fragment of plasmid pBR322trpSs to form plasmid pCLaHtrp-2.

The nucleotide and amino acid sequences of Fra-C-2 are shown below. The illustrative construction protocol of plasmid pCLaHtrp-2 is presented in FIG. 10.

```
Fra-C-2 (406 bp)
      ClaI           Met  Phe  Tyr  Phe  Asn  Lys  Pro  Thr  Gly
      CGATAAA—ATG—TTC—TAC—TTC—AAC—AAA—CCG—ACC—GGC—
           TATTT—TAC—AAG—ATG—AAG—TTG—TTT—GGC—TGG—CCG—

Tyr  Gly  Ser  Ser  Ser  Arg  Arg  Ala  Pro  Gln  Thr  Gly  Ile  Val  Asp
TAT—GGC—TCC—AGC—TCT—CGT—CGC—GCA—CCG—CAG—ACT—GGT—ATC—GTA—GAC—
ATA—CCG—AGG—TCG—AGA—GCA—GCG—CGT—GGC—GTC—TGA—CCA—TAG—CAT—CTG—

EcoRI
Glu  Gly  Gly  Asp  Glu  Phe  Met  Cys  Tyr  Cys  Gln  Asp  Pro  Tyr
GAG—GGT—GGC—GAT—GAA—TTC—ATG—TGT—TAC—TGC—CAG—GAC—CCA—TAT—
CTC—CCA—CCG—CTA—CTT—AAG—TAC—ACA—ATG—ACG—GTC—CTG—GGT—ATA—

10                                                    20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC  TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                       HindIII      60
Ser  Gln  Ile  Val  Ser  Phe  Tyr  Phe  Lys  Leu  Glu  Val  Glu
AGC—CAA—ATT—GTC—TCC—TTT—TAC—TTC—AAG—CTT—GAA—GTT—GAG—
TCG—GTT—TAA—CAG—AGG—AAA—ATG—AAG—TTC—GAA—CTT—CAA—CTC—

His  Glu  Phe  Gly  Met  Gly  Gly  Glu  Ala  Lys
CAT—GAA—TTC—GGT—ATG—GGC—GGT—GAA—GCT—AAA—
GTA—CTT—AAG—CCA—TAC—CCG—CCA—CTT—CGA—TTT—

Ser  Leu  Arg  Arg  Ser  Ser  Cys  Phe  Gly  Gly  Arg  Met  Asp  Arg
TCT—CTG—CGT—AGA—TCC—TCT—TGC—TTT—GGT—GGC—CGT—ATG—GAC—CGC—
AGA—GAC—GCA—TCT—AGG—AGA—ACG—AAA—CCA—CCG—GCA—TAC—CTG—GCG—

Ile  Gly  Ala  Gln  Ser  Gly  Leu  Gly  Cys  Asn  Ser  Phe  Arg  Tyr
ATC—GGT—GCT—CAG—TCC—GGT—CTG—GGC—TGT—AAC—TCT—TTC—CGT—TAC—
TAG—CCA—CGA—GTC—AGG—CCA—GAC—CCG—ACA—TTG—AGA—AAG—GCA—ATG— stop stop BamHI

TGA—TAG
ACT—ATC—CTA
```

A synthetic fd phage terminator-encoding gene (Fra-C-1) was ligated into the BamHI-SalI restriction fragment of plasmid pBR322 to form plasmid pter21. The plasmid pter21 was digested with restriction enzymes PstI and BamHI to obtain a DNA fragment containing the fd phage terminator-encoding DNA, and the latter was ligated to the large BamHI-PstI restriction fragment of plasmid pCLaHtrp-2 to form plasmid pCLaHtrp3t. The nucleotide and amino acid sequences of Fra-C-1 are shown below. The illustrative construction protocol of plasmid pCLaHtrp3t is presented in FIG. 11.

Fra-C-1 (47 bp) Synthetic fd phage terminator gene

GATCCTCGAGATCAATTAAAGGCTCCTTTTGGAGCCTTTTTTTTTG
    GAGCTCTAGTTAATTTCCGAGGAAAACCTCGGAAAAAAAAACAGCT

The previously described Fra-A-7 was ligated into the BamHI-HindIII restriction fragment of plasmid pCLaHtrp3t to form two-cistronic expression vector pCE-SM3t which encodes trp promoter III, Cd-LH, IGF-I and fd phage terminator. The illustrative construction protocol is presented in FIG. 12.

DNA fragment used for the construction of present expression vectors was conventionally prepared by annealing and ligating the oligonucleotides which were prepared in accordance with the method of Ito, H., Ike, Y., Ikuta, S. and Itakura, K., Nucleic Acids Research, 10, 1, 755(1982).

Although expression vectors of the invention can be applied to a wide range of E. coli host cells, E. coli K and E. coli B strains are most preferred as host cells. E. coli MM 294 is especially preferable. The present expression vector can be transformed into E. coli host cell using conventional methods such as Kushner's method. When the transformant is cultured under suitable conditions for growth, genes encoding Cd-LH and Met-IGF-I are expressed individually to produce each corresponding peptide. IGF-I is safely maintained inside of the host cell by virtue of the protective action of Cd-LH. Preferred cultivation methods are well known. E. coli is usually grown under aerobic culture conditions (e.g., shaking culture or submerged liquid culture) in nutrient medium containing assimilable carbon and nitrogen sources. Preferred carbon sources in a culture medium include, for example, carbohydrates such as glucose, fructorse, sucrose, glycerol, and starch. Other carbon sources may include xylose, galactose, maltose, dextrin, and lactose.

Preferred nitrogen sources include, for example, yeast extract, peptone, gluten meal, cottonseed meal, soybean meal, corn steep liquor, dried yeast, and malt of wheat. Inorganic and organic nitrogen compounds such as ammonium nitrate, ammonium sulfate, ammonium phosphate, urea, and amino acids can be also included in the culture medium.

It is not necessarily required to use these carbon and nitrogen sources in a purified form, since relatively impure materials often contain a trace amounts of essential elements required for the growth and considerable amounts of inorganic nutrients, and therefore, they are also suitable for cultivation. If desired, inorganic salts such as calcium bicarbonate, sodium or potassium phosphate, sodium or potassium chloride, magnesium or cupric salts may be added into the culture medium.

Mixing of the culture medium can be accomplished using mechanical stirrers such as propeller or various devices with pump, or by rotating or shaking the fermenter, or aerating sterilized air into the culture medium. Fermentation are usually conducted at temperature ranging from about 20° to 42° C., preferably about 35°–38° C., for several hours to 50 hours.

The expressed Met-IGF-I is retained inside of transformants together with Cd-LH, probably in an associated form. The associated Met-IGF-I can be easily recovered from the culture medium using conventional methods. Generally, it can be conducted as follows. Transformed cells are collected by filteration or centrifugation and lysed by vacuum concentration or ultrasonification. From the resultant lysate, the desired Met-IGF-I can be isolated using HPLC, lyophylization, pH adjustments, adsorption on appropriate resins such as anionic, cathionic, or nonionic resins, adsorbents (e.g., carbon, silic acid, silica gel, cellulose, or alumina), gel filteration, recrystallization from suitable solvents or combination thereof. In the illustrative example, the lysate is dialysed against 1N acetic acid to separate soluble Met-IGF-I from insoluble Cd-LH, and the dialyzed solution is subjected to purification process.

The present invention provides for an efficient means for producing a large amount of Met-IGF-I in purified form as compared with conventional methods. Met-IGF-I provided by the present invention is useful for the treatment of various diseases caused by disorder of proliferation or growth of bone cells, or other diseases such as osteoporosis, deabetes, wound or ulcer. Met-IGF-I can be formulated into a pharmaceutical composition suitable for oral or parenteral administration in accordance with conventional methods known to the art.

In the accompanying drawings:

FIG. 1 shows the nucleotide and amino acid sequence of Met-IGF-I.

Figure 5:
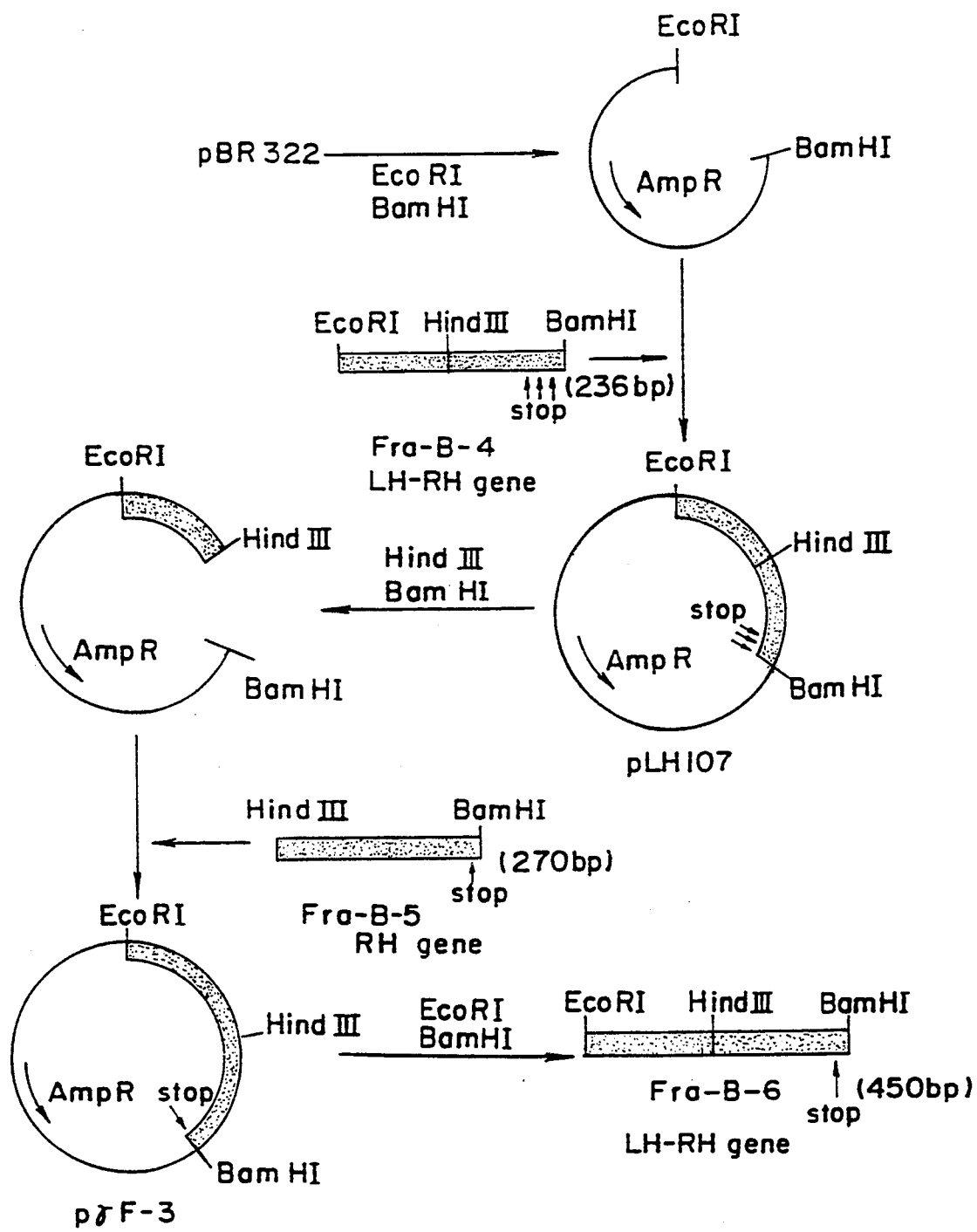
Figure 5B:
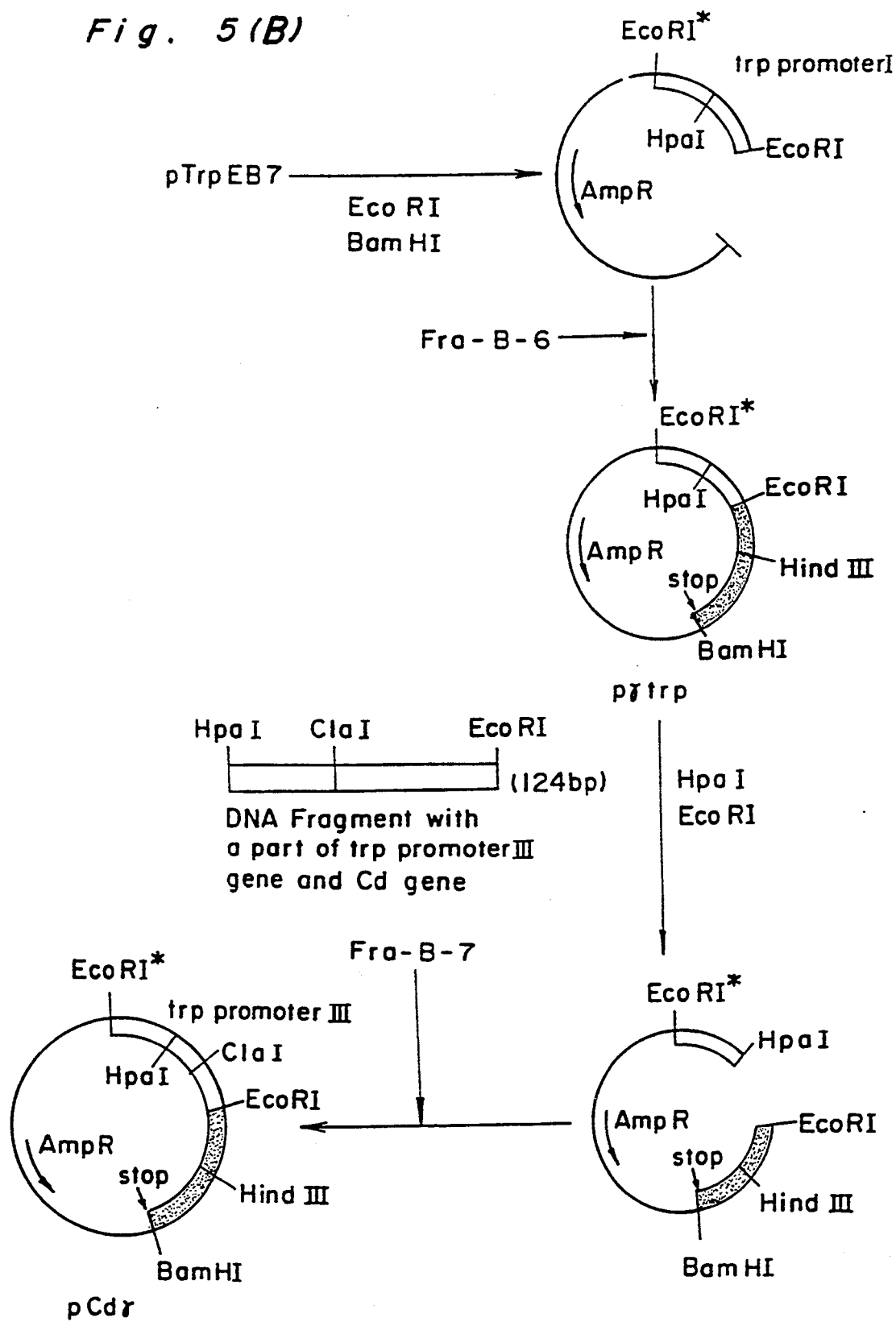

FIGS. 5 (1)–5 (2) are a schematic illustration of the construction protocol for plasmid pCdγ.

Figure 6:
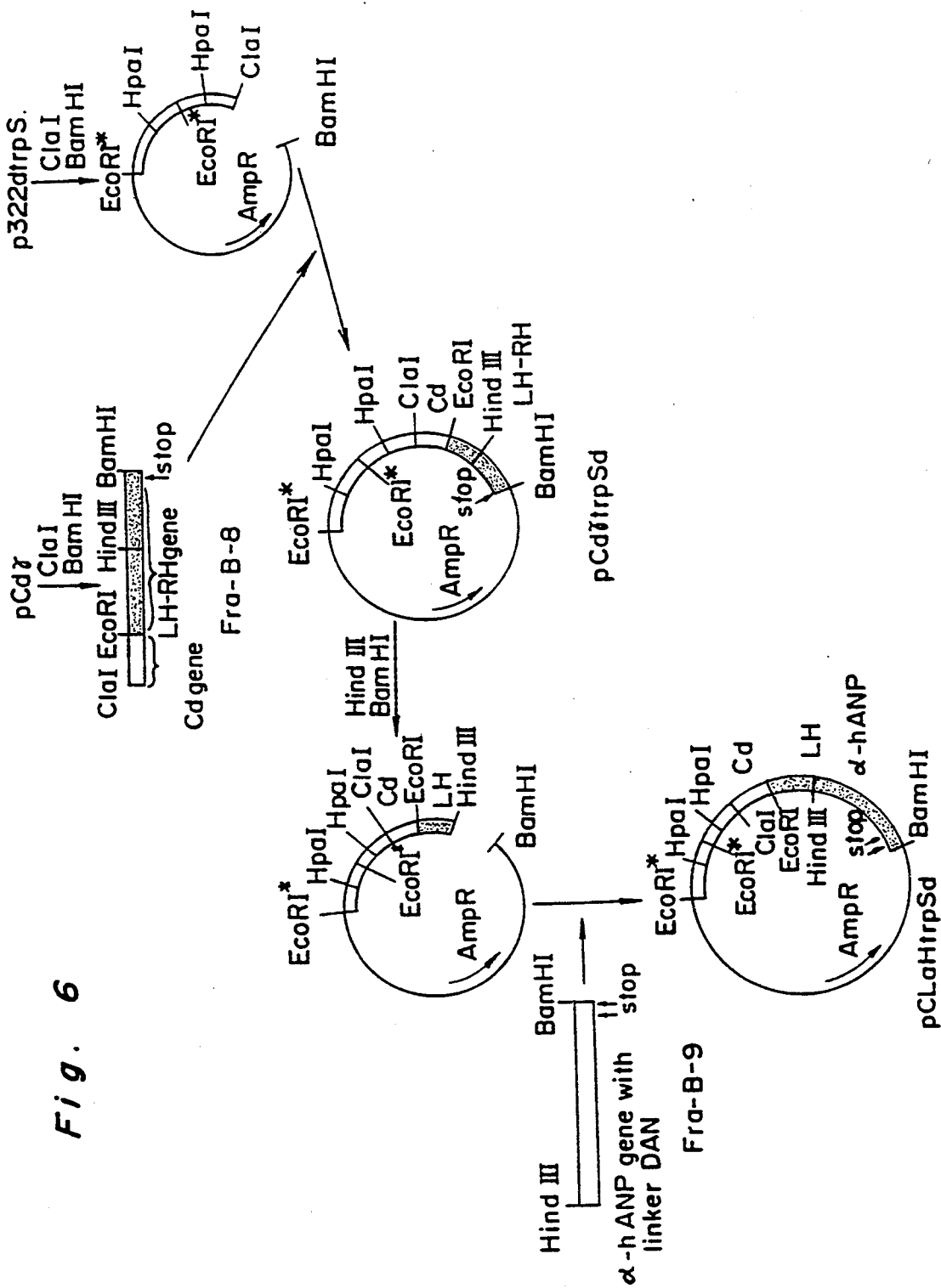

FIG. 6 is a schematic illustration of the construction protocol for plasmid pCLaHtrpSd.

Figure 7A:
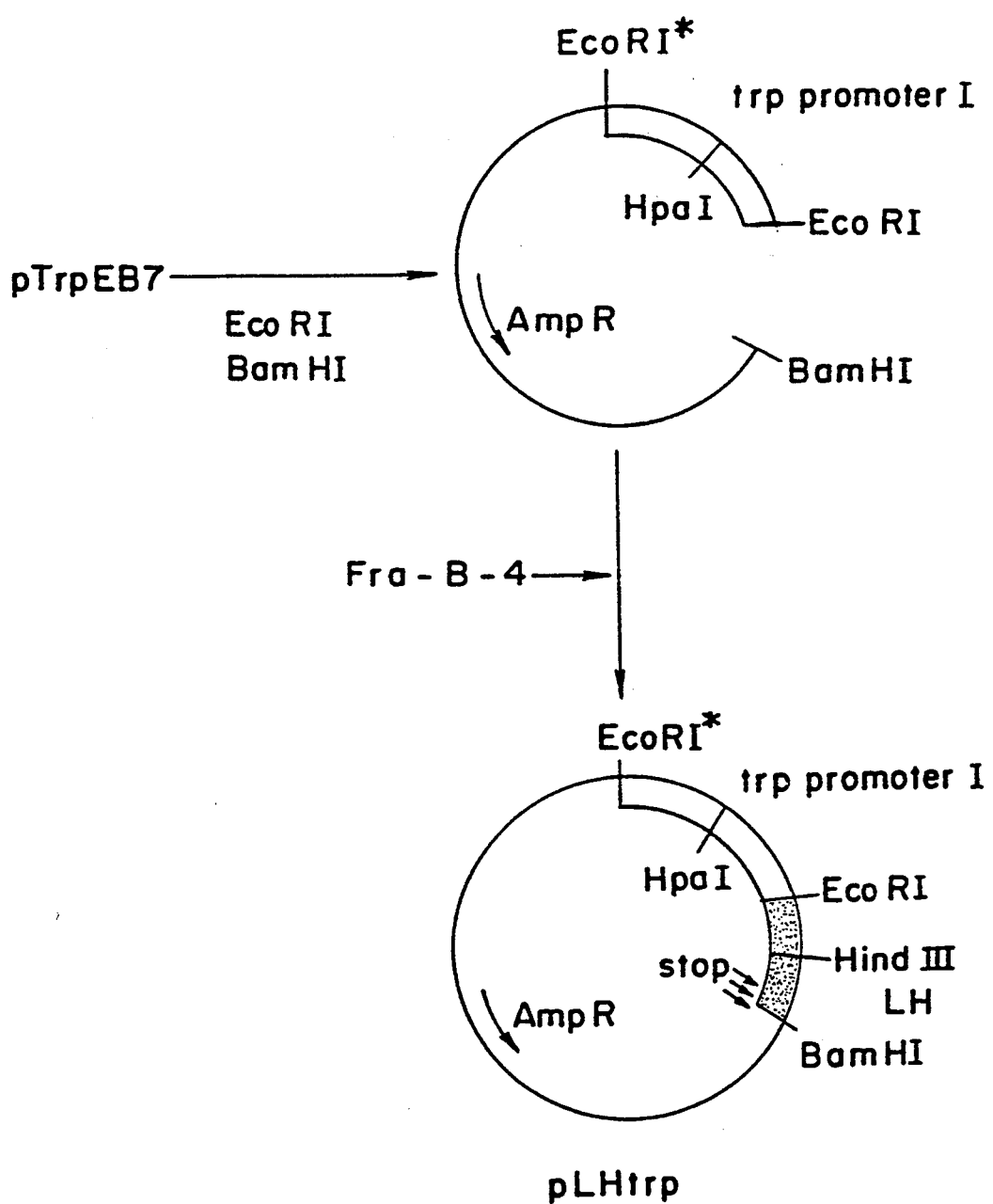
Figure 7:
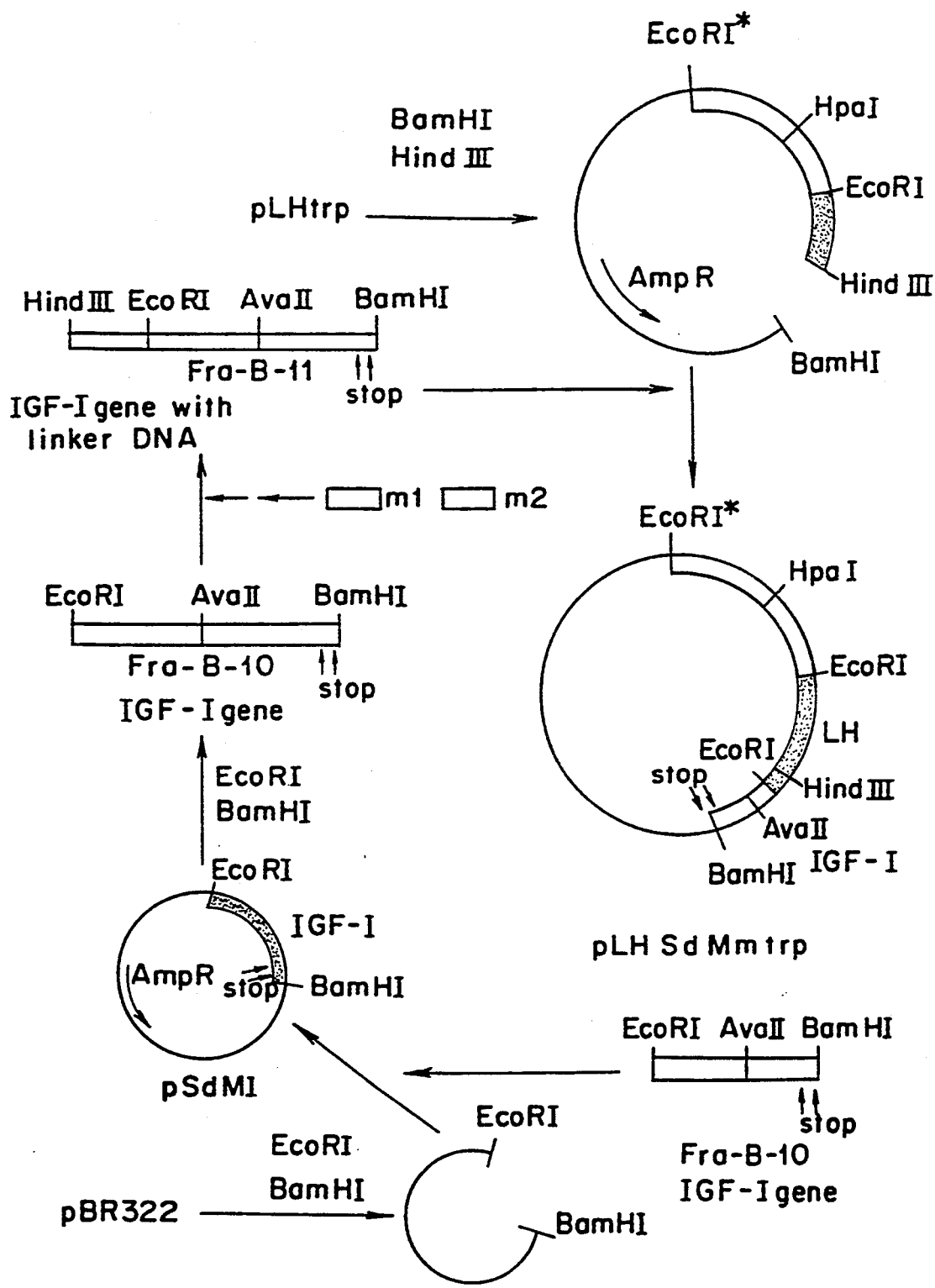

FIGS. 7 (1)–7 (2) are a schematic illustration of the construction protocol for plasmid pLHSdMmtrp.

Figure 8:
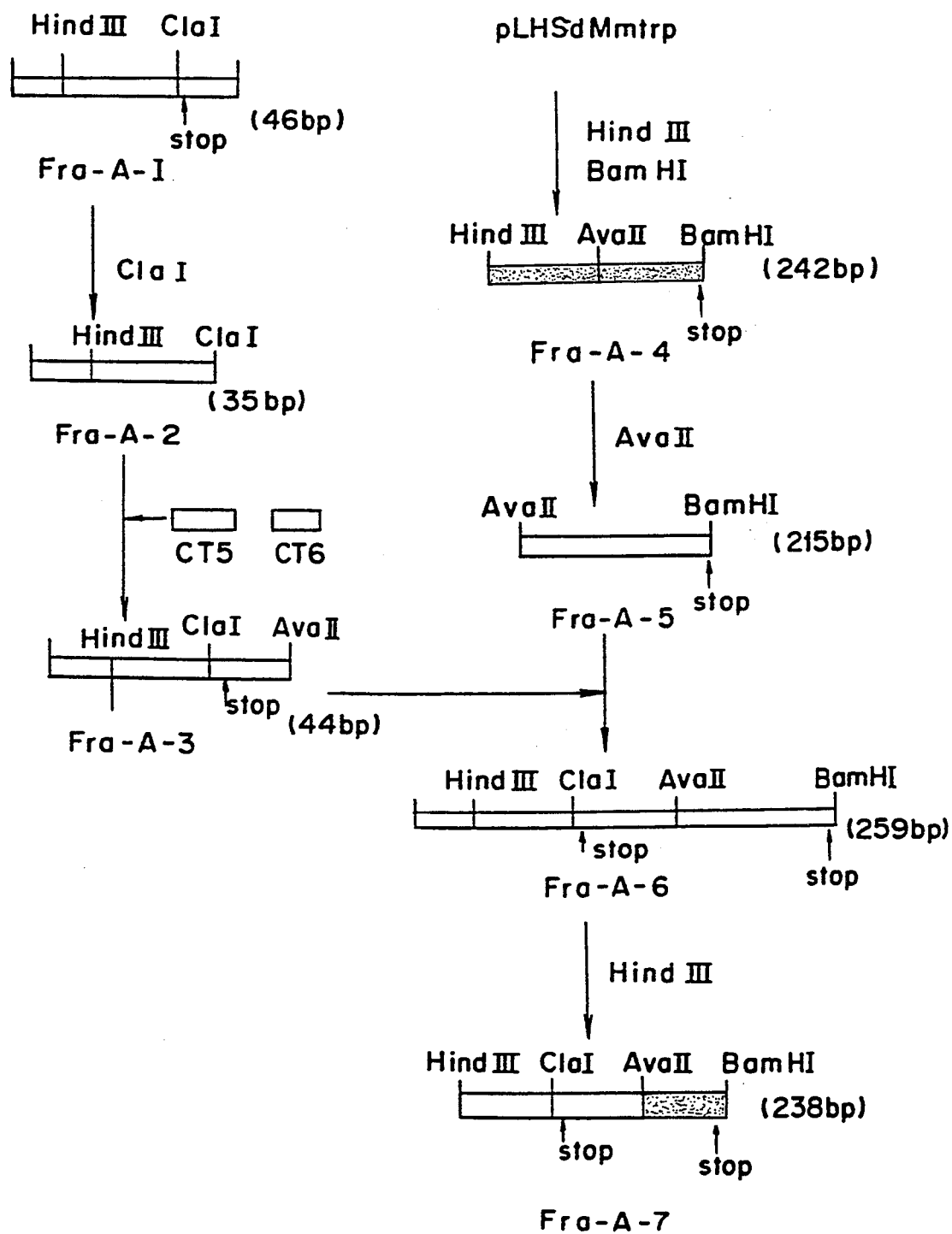

FIG. 8 is a schematic illustration of the synthesis protocol for DNA fragment (Fra-A-7) used for the construction of two-cistronic expression vector.

Figure 9:
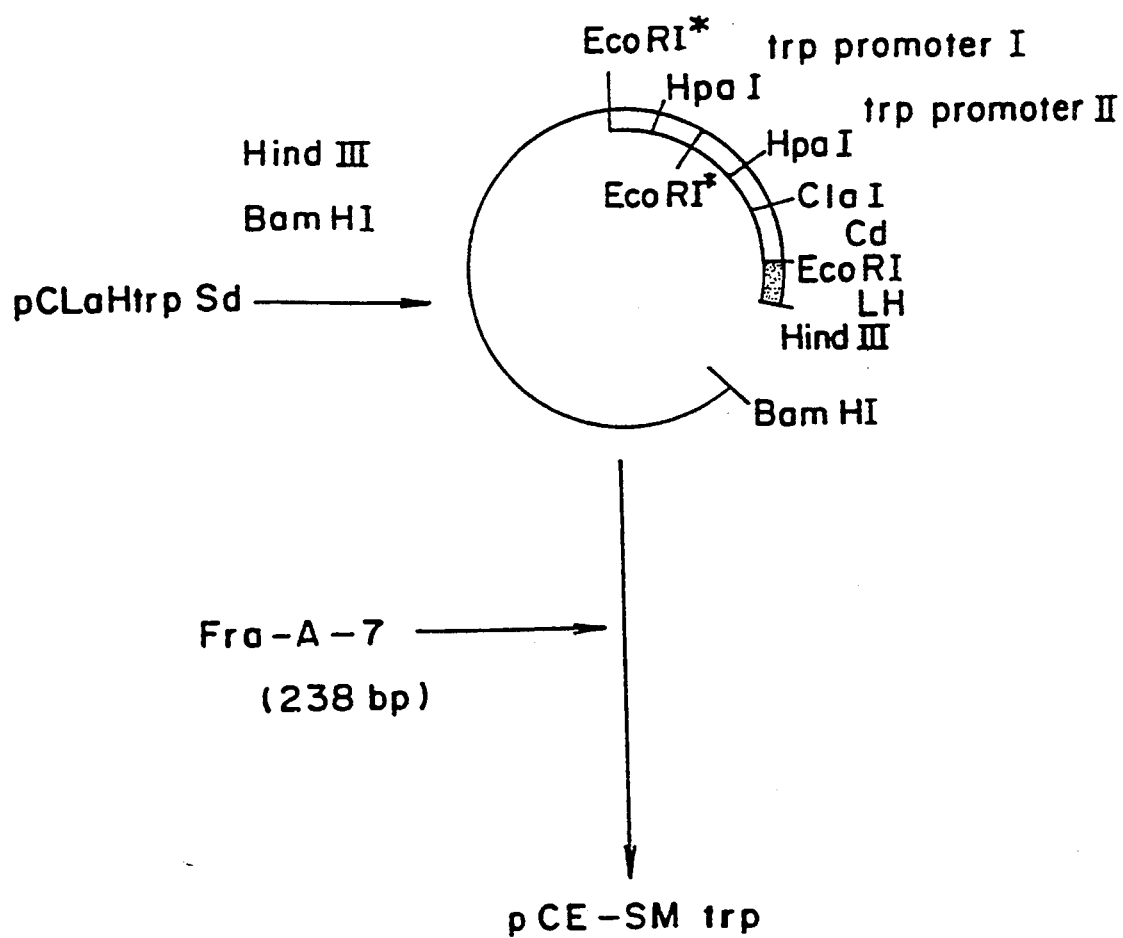

FIG. 9 is a schematic illustration of the construction protocol for plasmid pCE-SMtrp.

Figure 10:
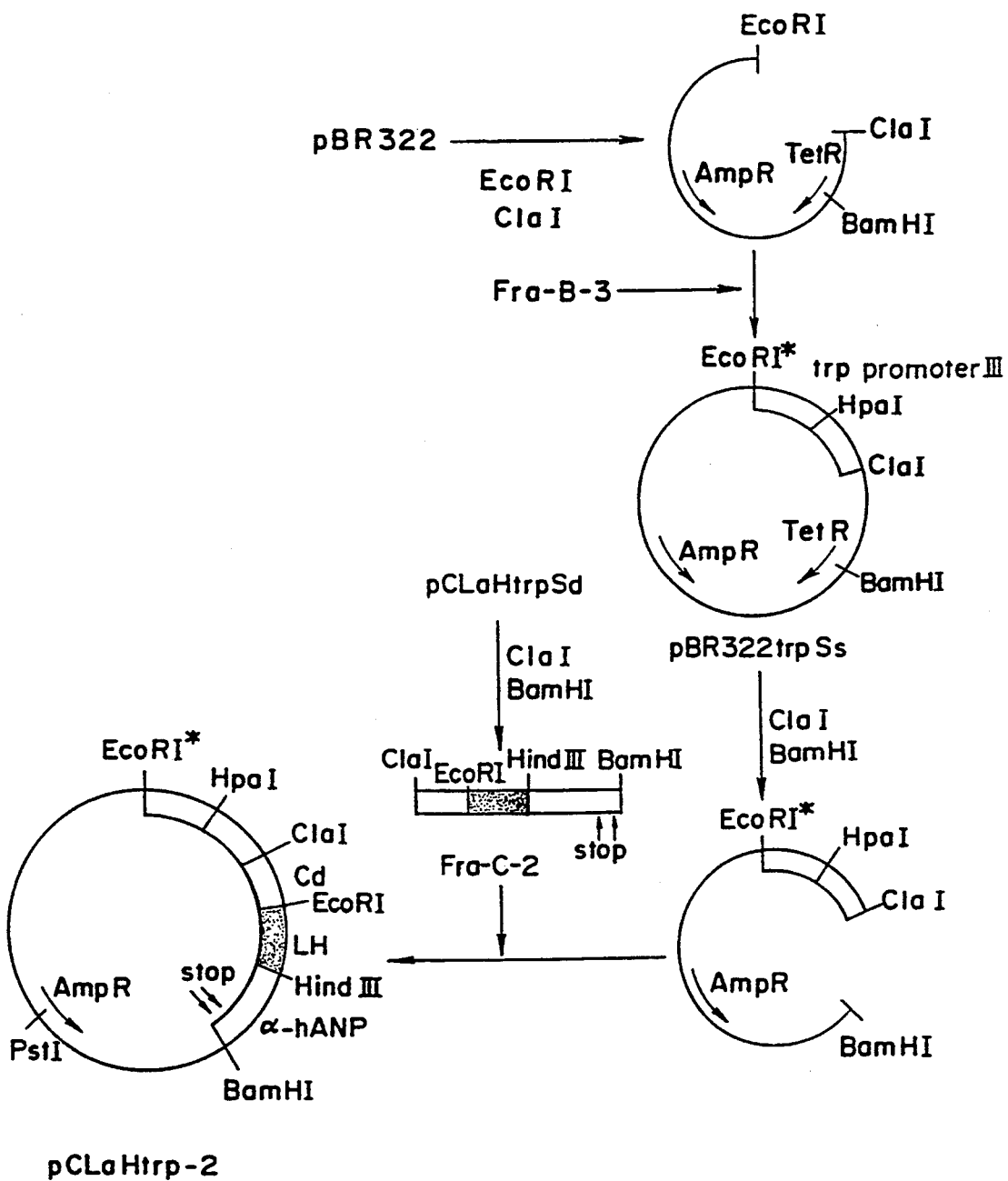

FIG. 10 is a schematic illustration of the construction protocol for plasmid pCLaHtrp-2.

Figure 11:
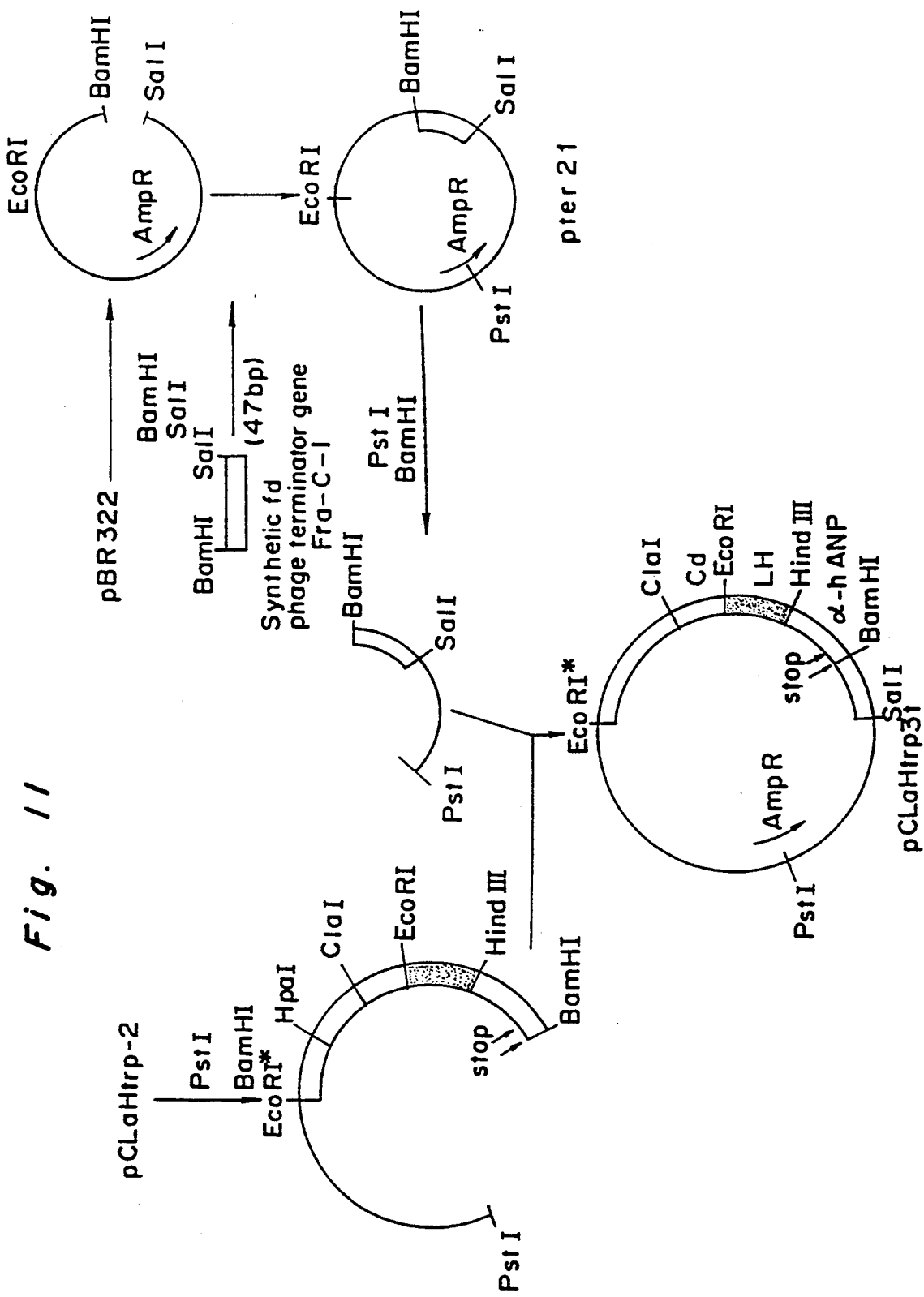

FIG. 11 is a schematic illustration of the construction protocol for plasmid pCLaHtrp3t.

Figure 12:
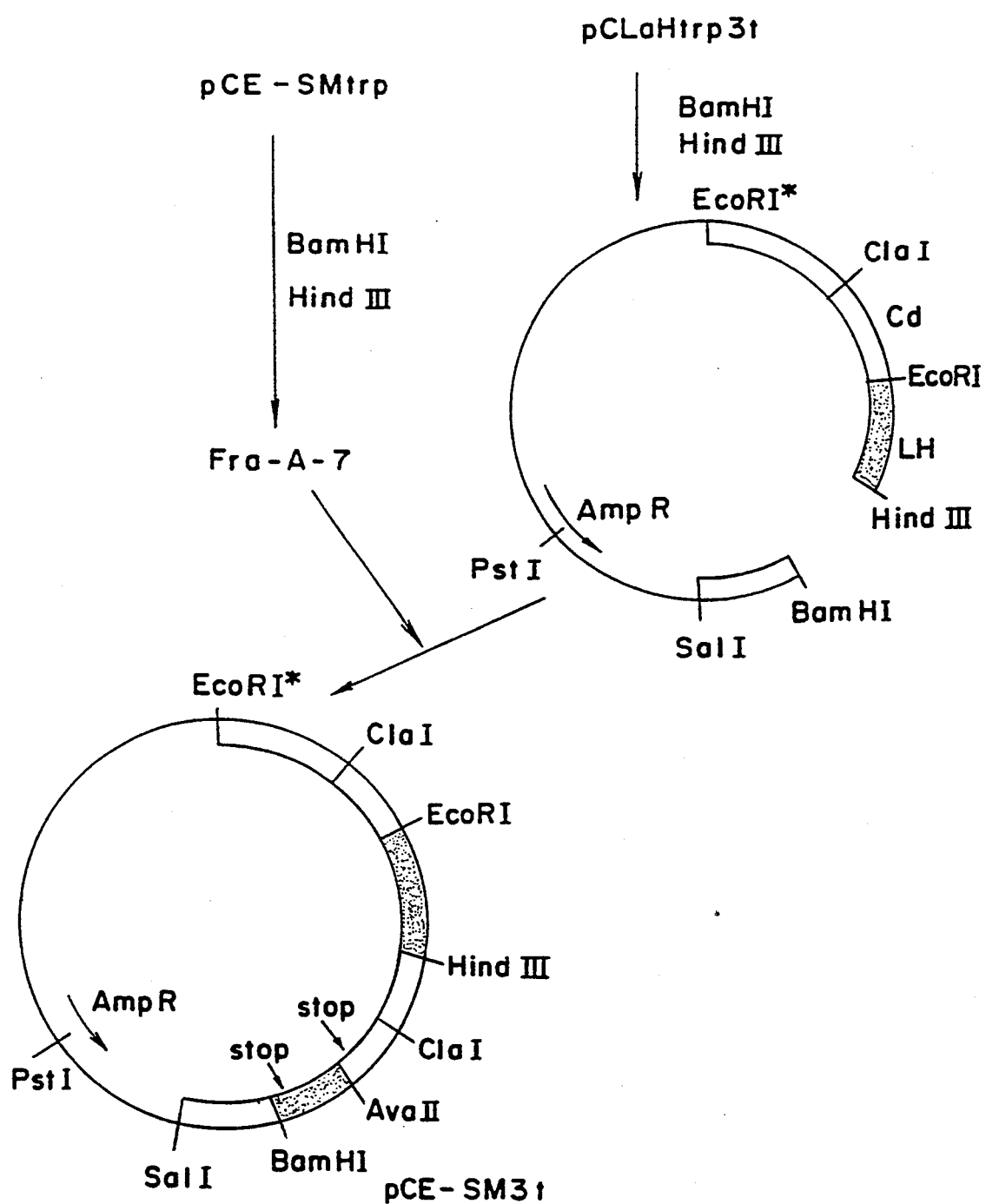

FIG. 12 is a schematic illustration of the construction protocol for plasmid pCE-SM3t.

Figure 13:
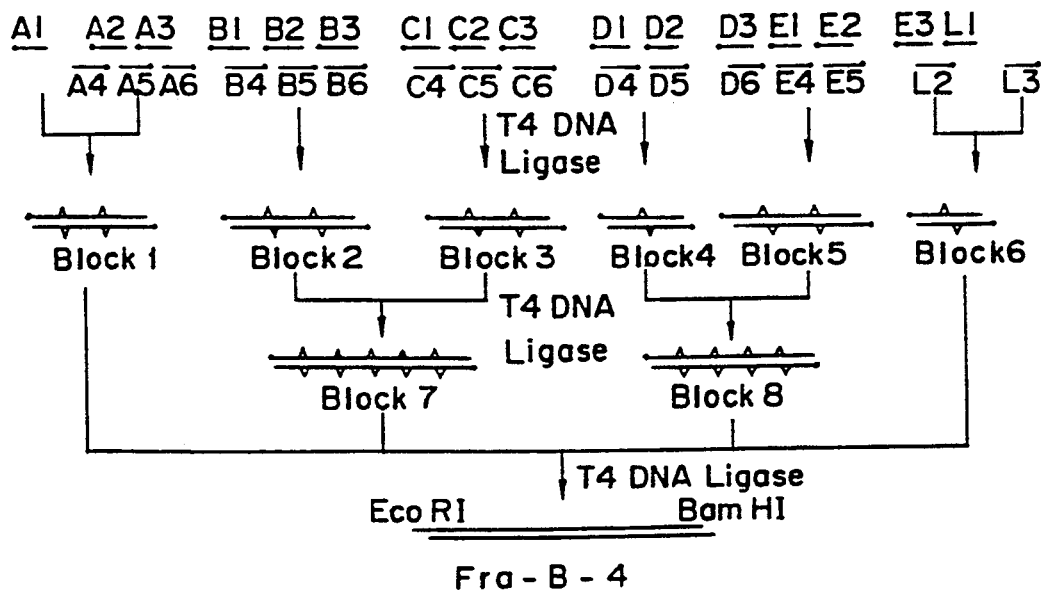
Figure 13:
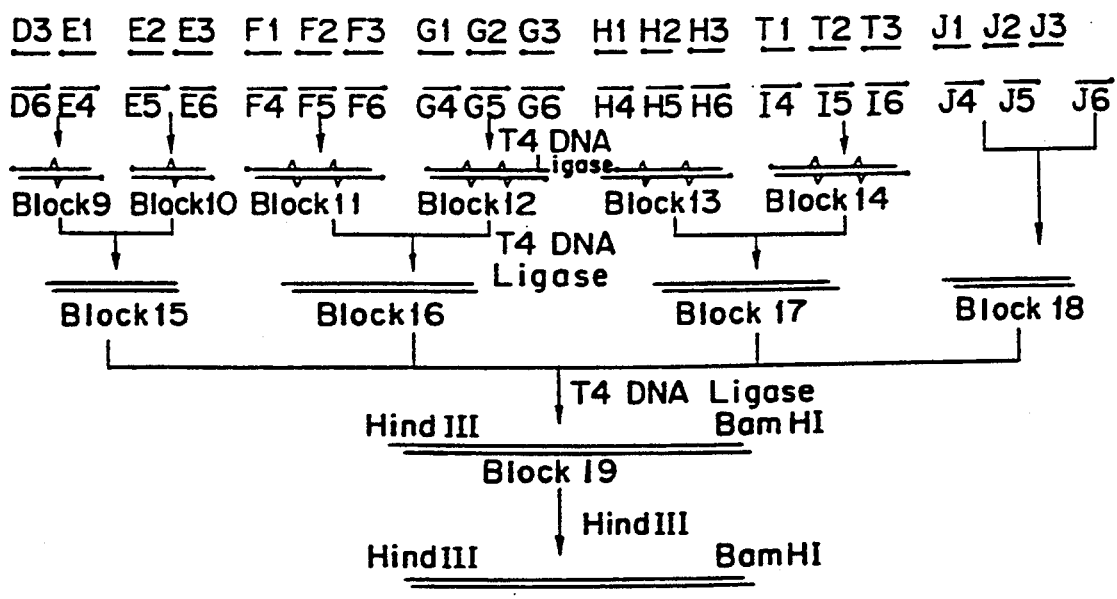

FIGS. 13 (1) and 13 (2) are a schematic illustration of the synthesis protocol for DNA fragments encoding LH and RH (Fra-B-4 and Fra-B-5).

Figure 14:
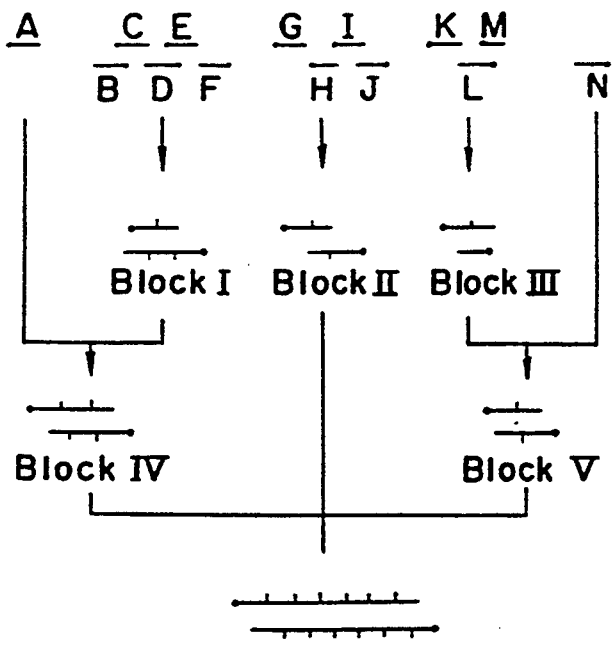

FIG. 14 is a schematic illustration of the synthesis protocol for Fra-B-1.

Figure 15:
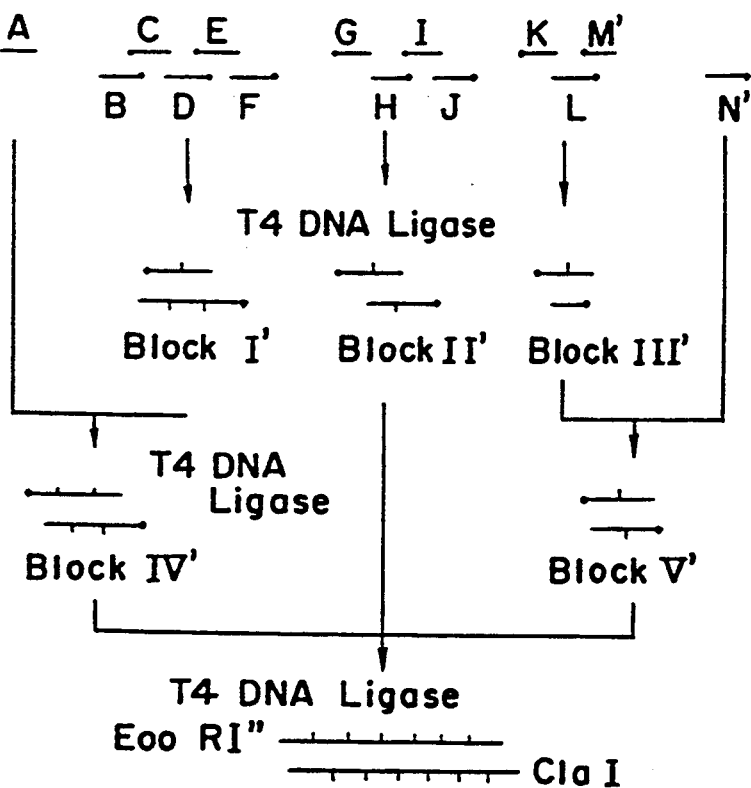

FIG. 15 is a schematic illustration of the synthesis protocol for Fra-B-3.

Figure 16:
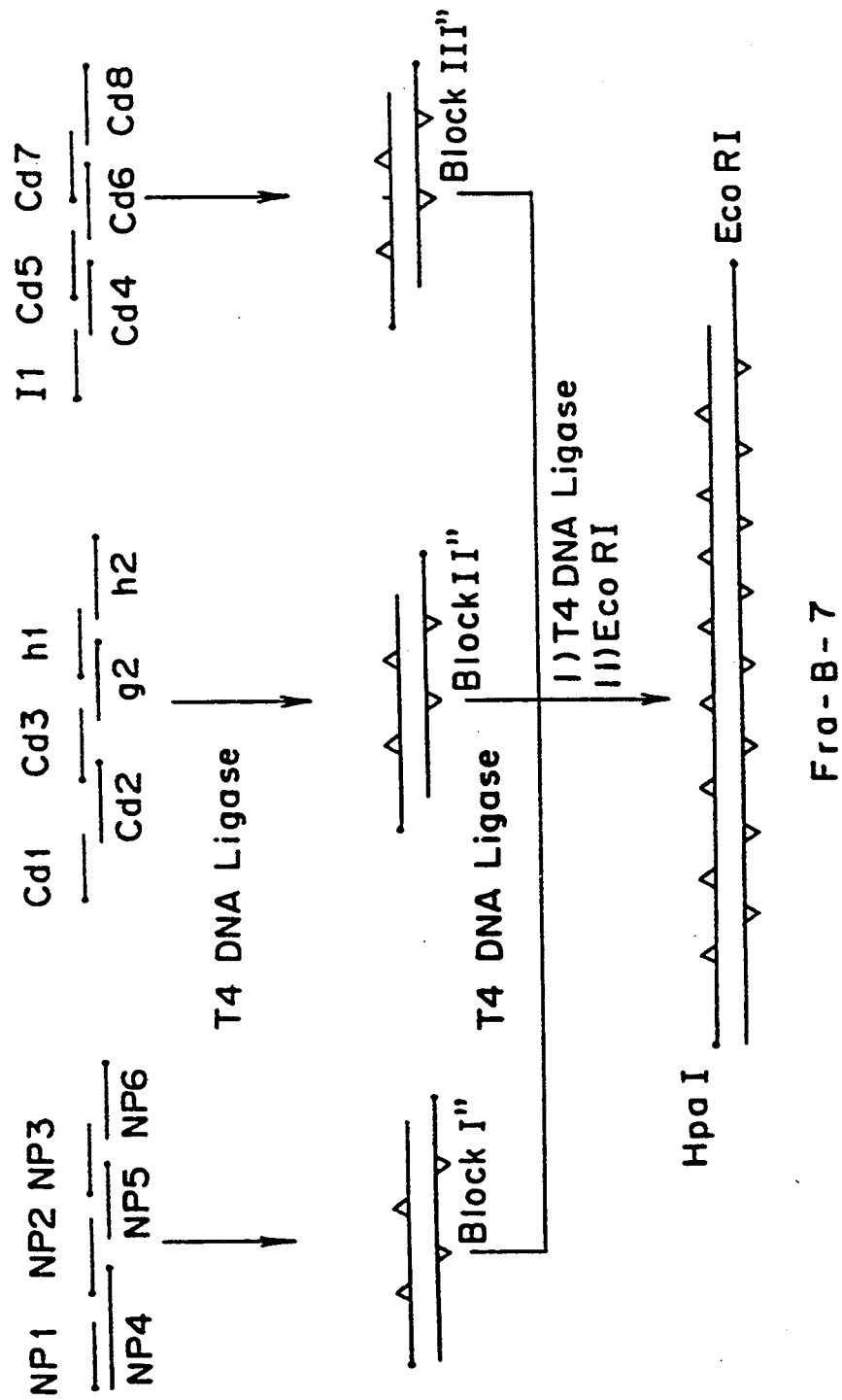

FIG. 16 is a schematic illustration of the synthesis protocol for Fra-B-7.

Figure 17:
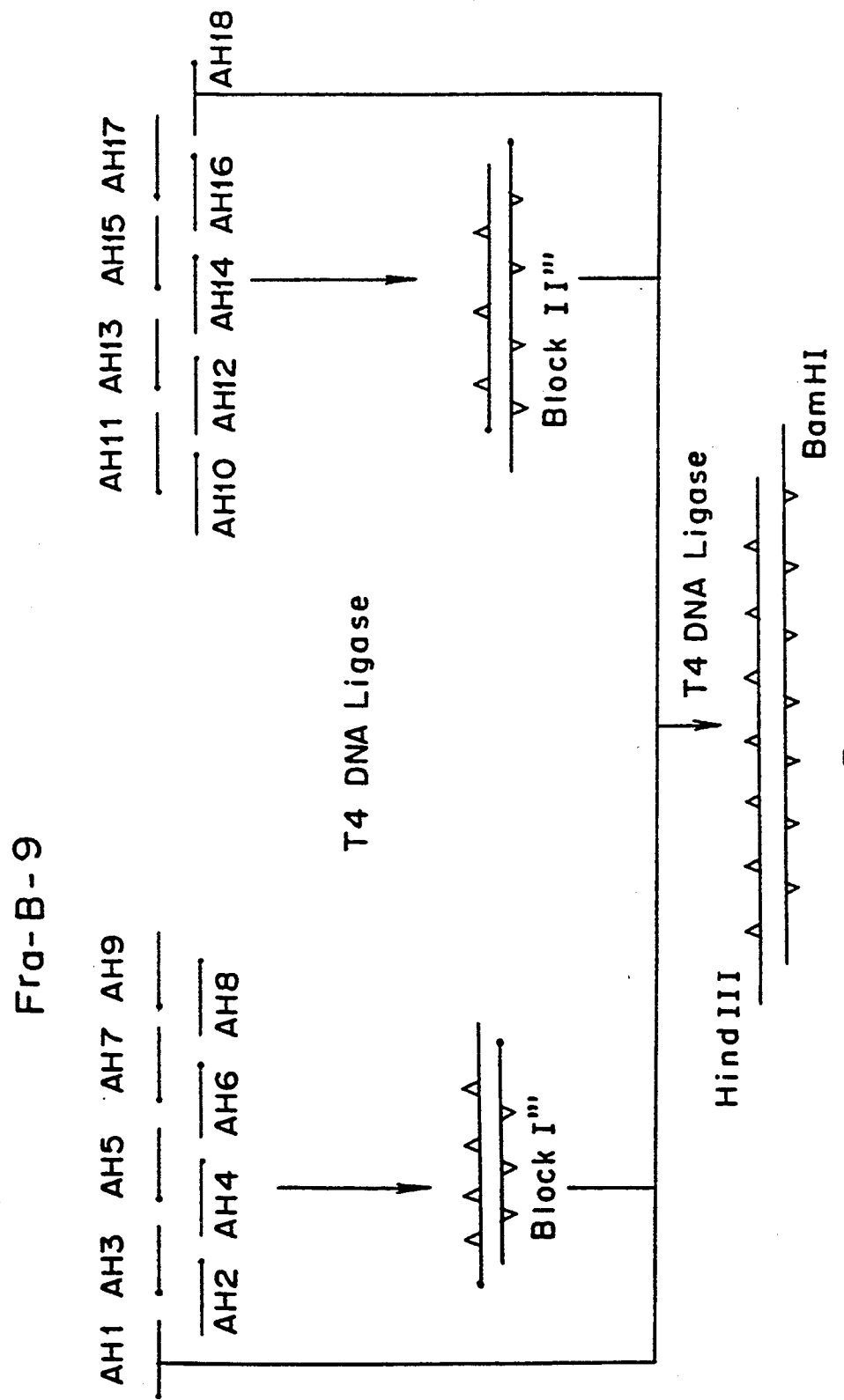

FIG. 17 is a schematic illustration of the synthesis protocol for Fra-B-9.

Figure 18:
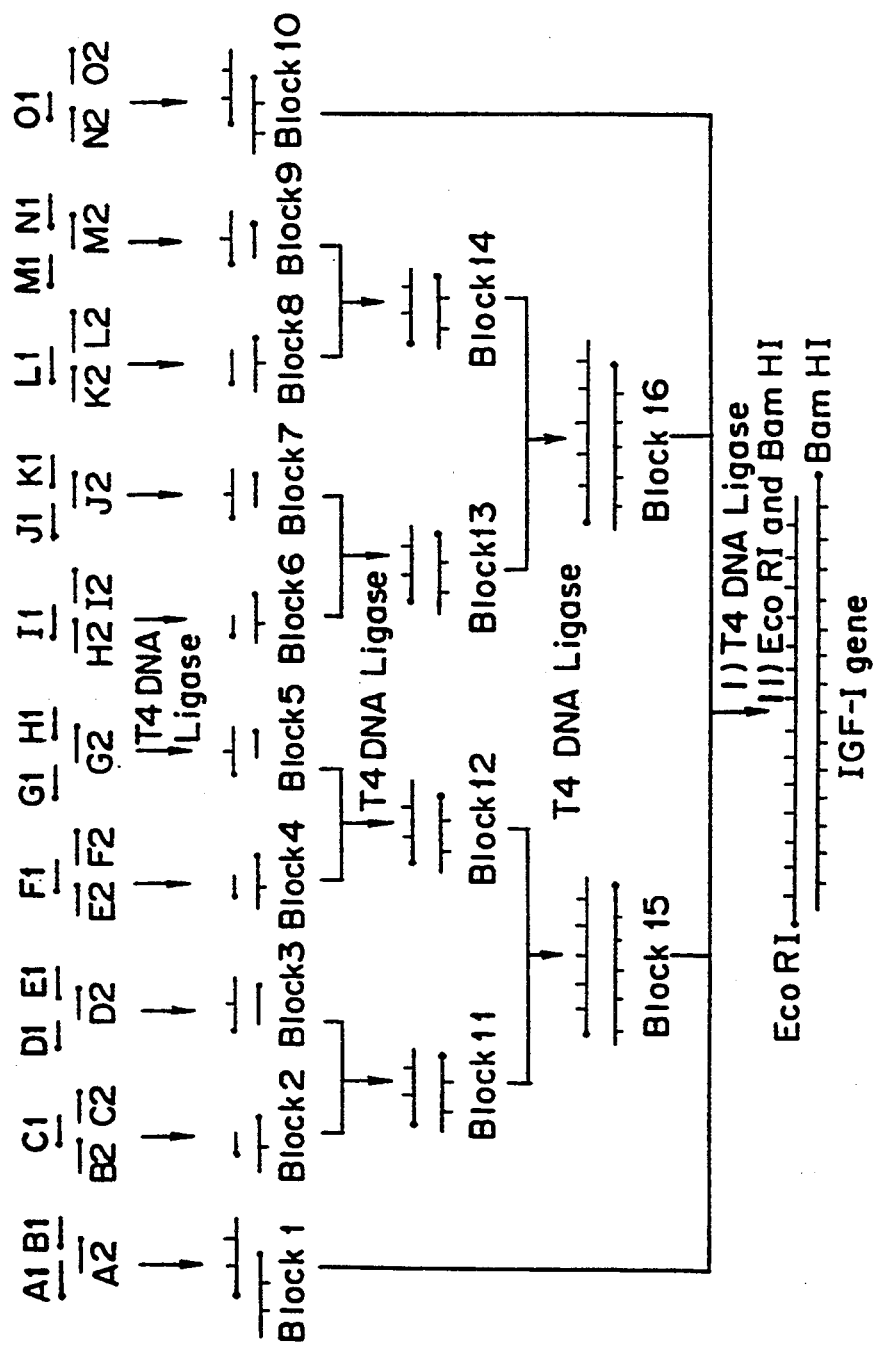

FIG. 18 is a schematic illustration of the synthesis protocol for Fra-B-10.

Figure 19A:
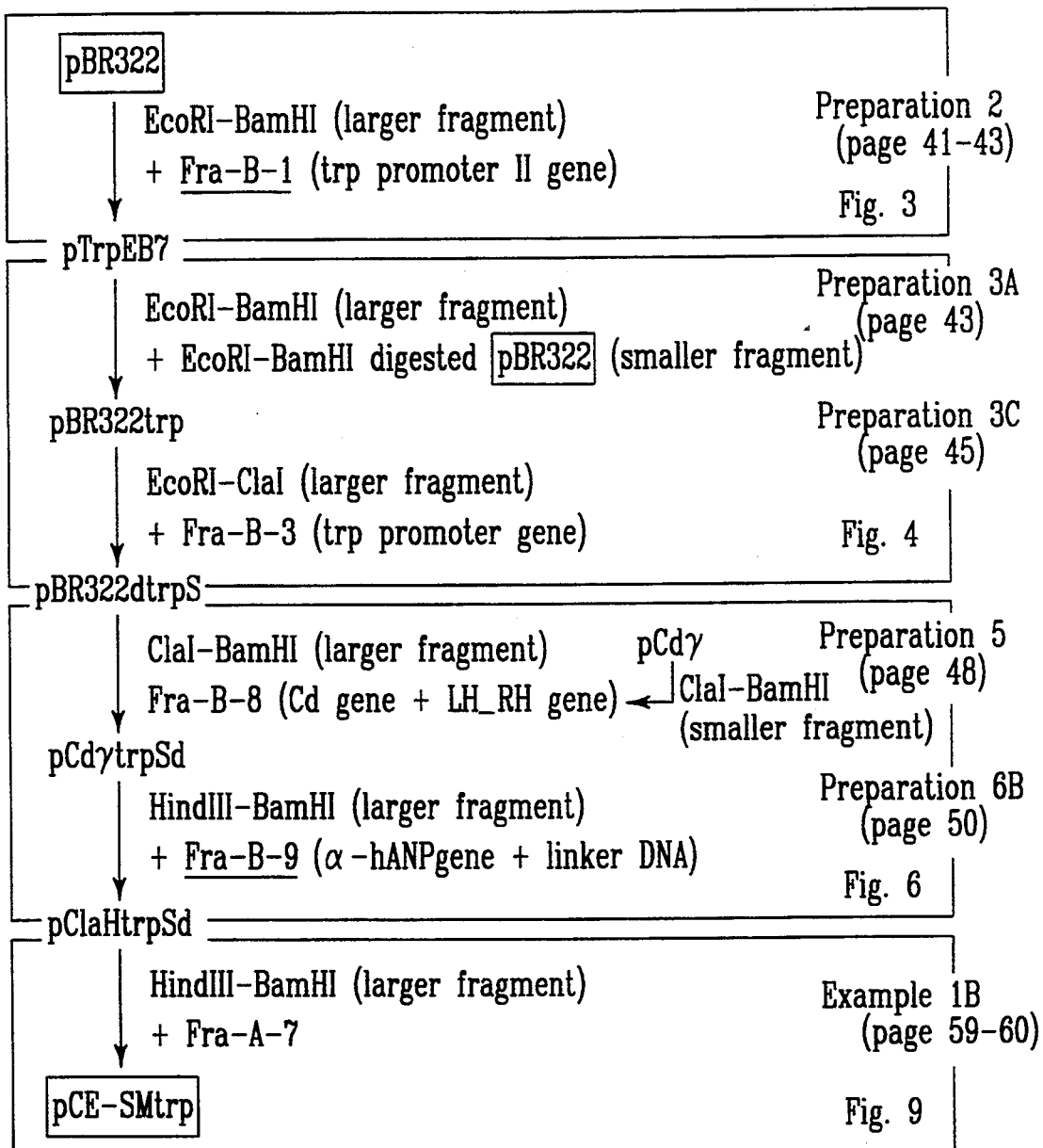
Figure 19B:
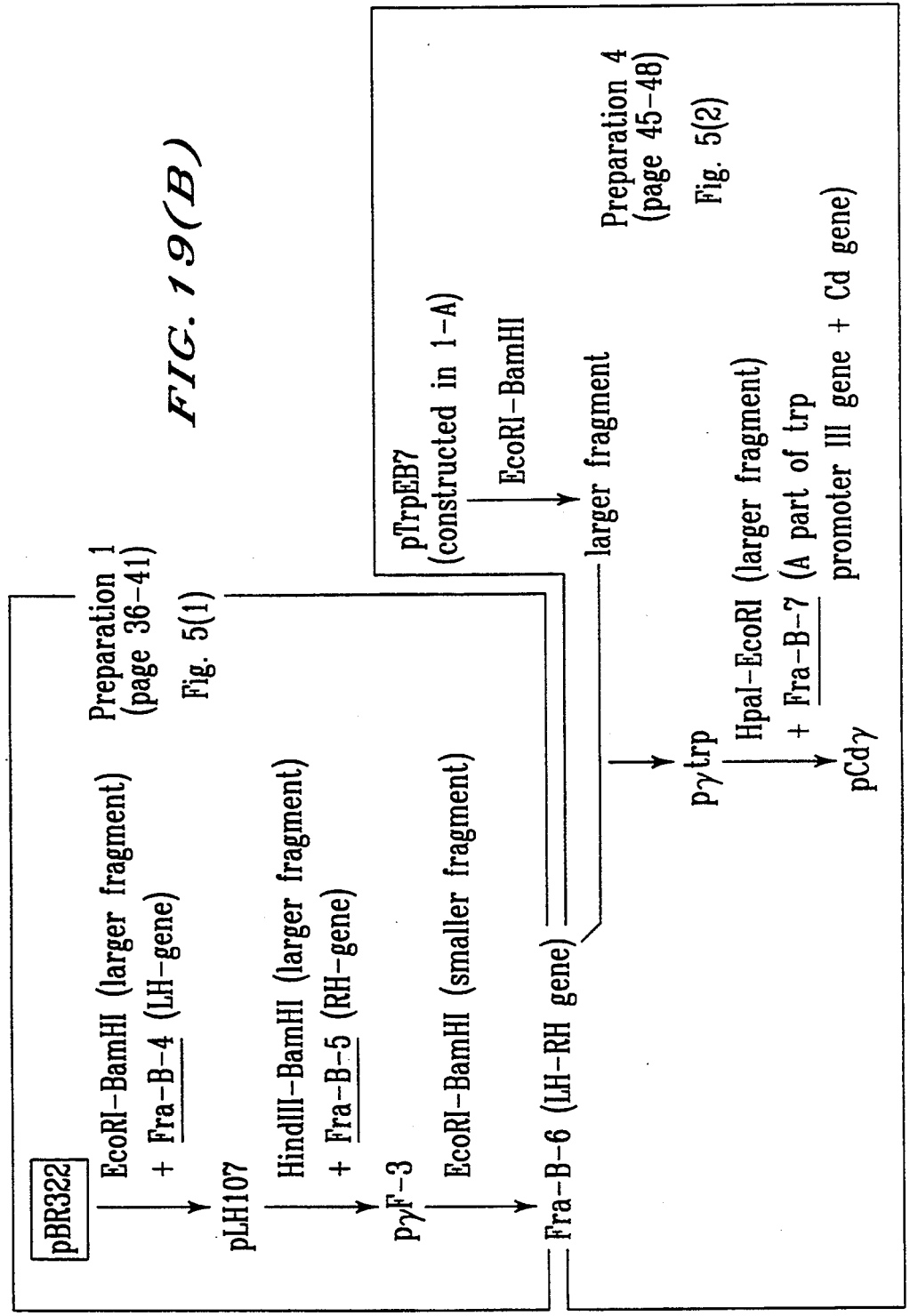
Figure 19C:
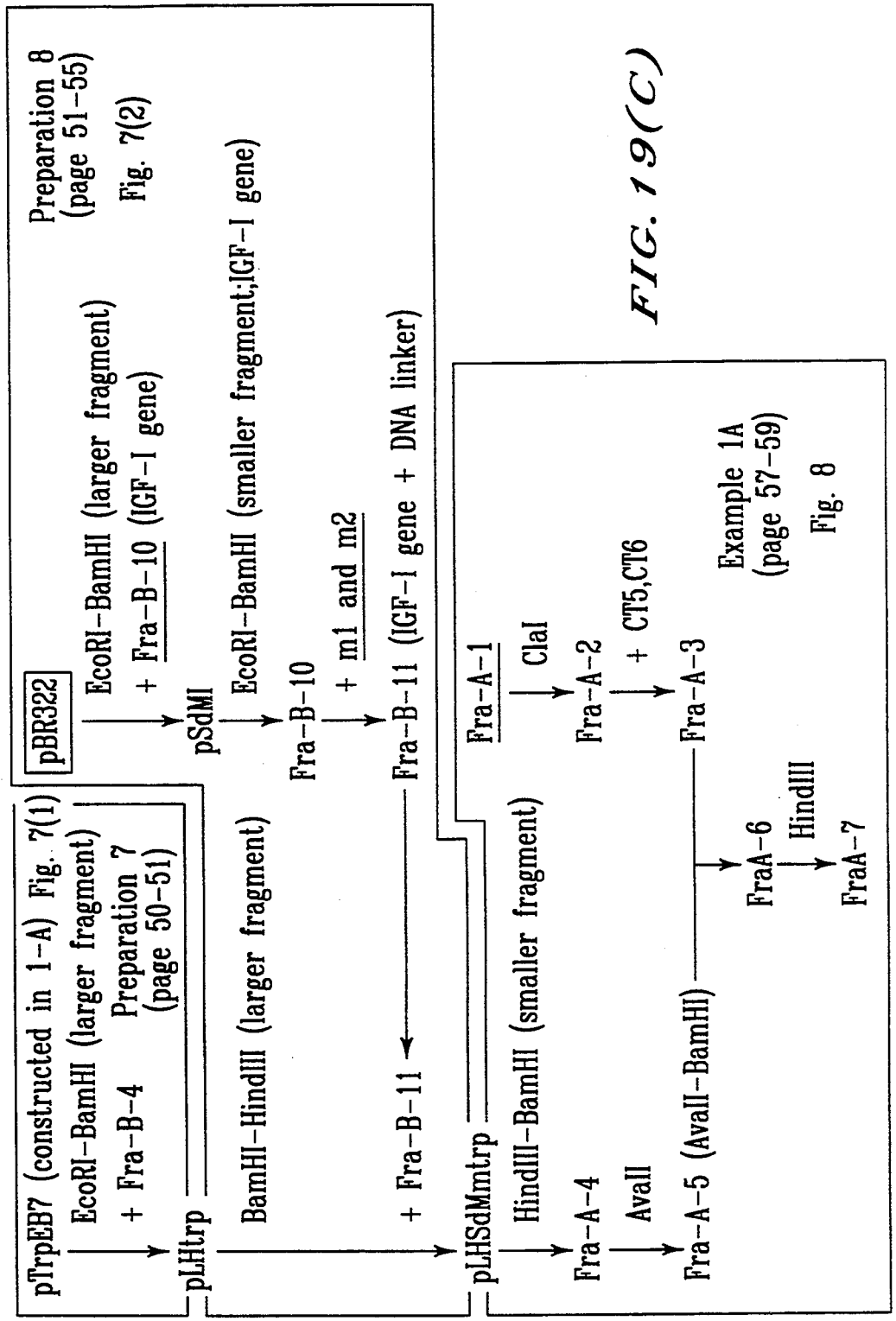

FIG. 19 (A) is a schematic illustration of the construction of pCE-SMtrp.

FIG. 19 (B) is a schematic illustration of the construction of pCd7.

FIG. 19 (C) is a schematic illustration of the construction of FRA-7.

Figure 20A:
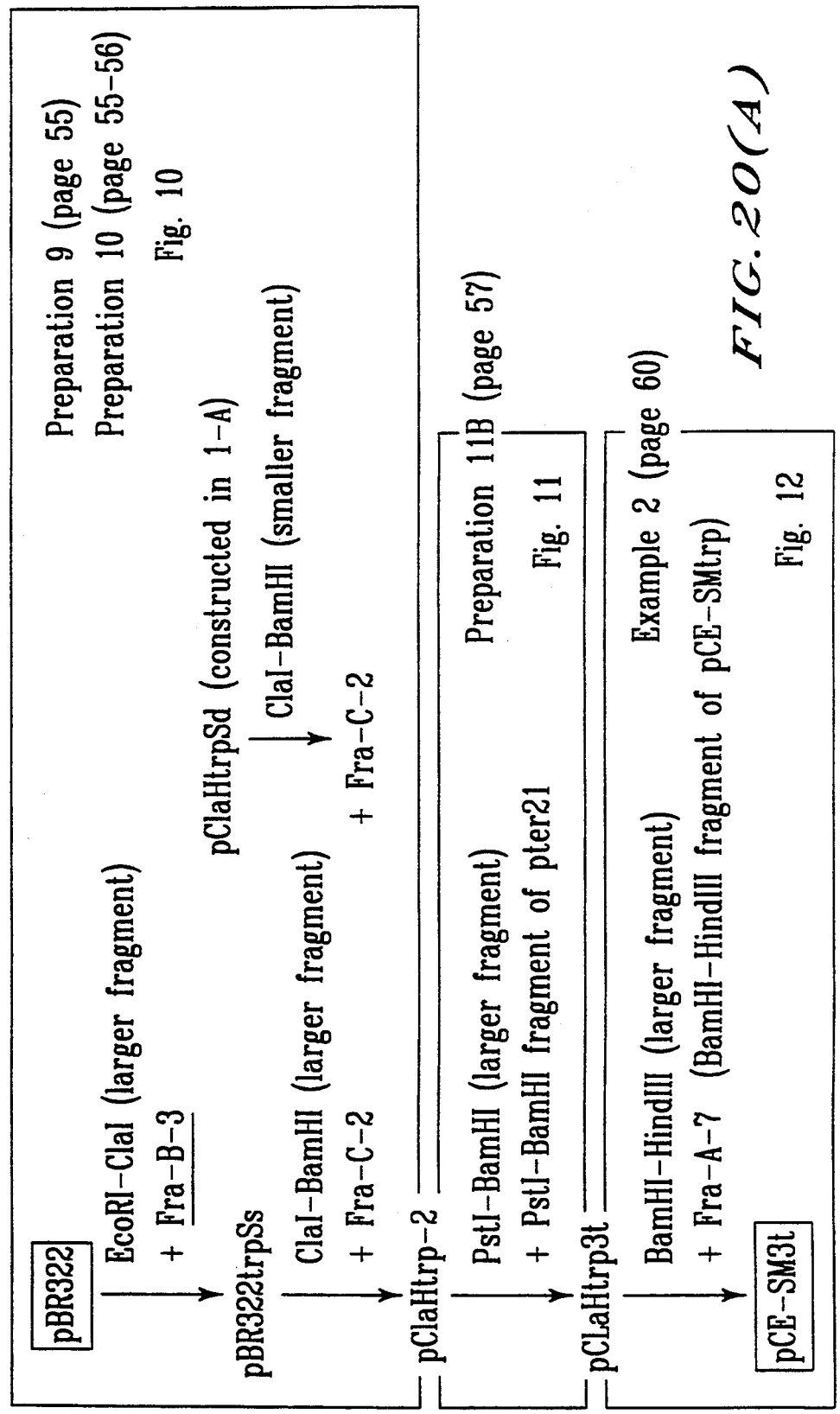
Figure 20B:
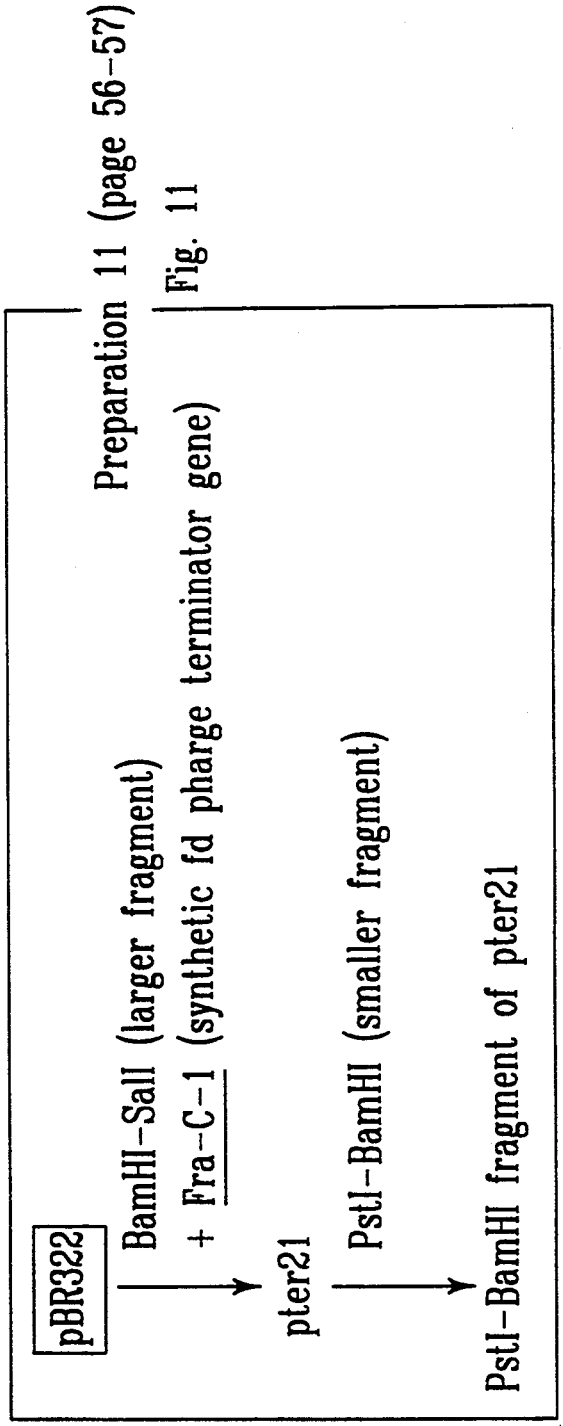

FIG. 20 (A) is a schematic illustration of the construction of pCE-SM3t.

FIG. 20 (B) is a schematic illustration of the construction of the pstI-BamHI fragment of pter21.

The following preparations and examples further illustrate the invention.

DNA oligomers used for the synthesis of DNA fragments in the following preparations and examples were prepared in substantial accordance with the procedure of Ito, S. et al., (1982), Nucleic Acids Research, 10 175. The DNA fragments can also be synthesized by the modified phosphotriester method using protected deoxyribonucleotide building blocks.

Unless otherwise stated, the isolation of a desired DNA fragment from a plasmid was accomplished by digesting said plasmid with restriction enzyme(s) and separating the desired fragment from the digestion mixture using polyacrylamide gel electrophoresis.

Preparation 1

Preparation of Gene Encoding LH-RH (Fra-B-6)

For the preparation of Fra-B-4 and Fra-B-5 (oligonucleotides for IFN LH gene and IFN RH gene), the 63 oligonucleotides were synthesized using conventional methods.

| | | |
|---|---|---|
| (1) HOApApTpTpCpApTpGpTpGpTpTOH | (a1) |
| (2) HOApCpTpGpCpCpApGpGpApCpCpCpApTOH | (a2) |
| (3) HOApTpGpTpApApApApGpApApGpCpApGOH | (a3) |
| (4) HOTpGpGpCpApGpTpApApCpApCpApTpGOH | (a4) |
| (5) HOTpTpTpApCpApTpApTpGpGpGpTpCpCOH | (a5) |
| (6) HOApApGpGpTpTpTpTpCpTpGpCpTpTpCpTOH | (a6) |
| (7) HOApApApApCpCpTpTpApApGpApApApTpAOH | (b1) |
| (8) HOCpTpTpTpApApTpGpCpApGpGpTpCpAOH | (b2) |
| (9) HOTpTpCpApGpApTpGpTpApGpCpGpGpAOH | (b3) |
| (10) HOApTpTpApApApApGpTpApTpTpTpCpTpTOH | (b4) |
| (11) HOApTpCpTpGpApApTpGpApCpCpTpGpCOH | (b5) |
| (12) HOTpTpCpCpApTpTpApTpCpCpGpCpTpApCOH | (b6) |
| (13) HOTpApApTpGpGpApApCpTpCpTpTpTpTpCOH | (c1) |
| (14) HOTpTpApGpGpCpApTpTpTpTpGpApApGOH | (c2) |
| (15) HOApApTpTpGpGpApApApApGpApGpGpApGOH | (c3) |
| (16) HOTpGpCpCpTpApApGpApApApApApGpApGOH | (c4) |
| (17) HOTpCpCpApApTpTpCpTpTpCpApApApAOH | (c5) |
| (18) HOCpTpGpTpCpApCpTpCpTpCpCpTpCpTpTOH | (c6) |
| (19) HOApGpTpGpApCpApGpApApApApApTpAOH | (d1) |
| (20) HOApTpGpCpApGpApGpCpCpApApApApTpTOH | (d2) |
| (21) HOGpTpCpTpCpCpTpTpTpTpApApCpTpTOH | (d3) |
| (22) HOCpTpCpTpGpCpApTpTpApApTpTpTpTpTOH | (d4) |
| (23) HOApGpGpApGpCpApApApTpTpTpGpGOH | (d5) |
| (24) HOApApApGpCpTpTpGpApApGpTpApApAOH | (d6) |
| (25) HOCpApApGpCpTpTpTpTpCpApApApApApAOH | (e1) |
| (26) HOCpTpTpTpApApGpGpApTpGpApCpCpAOH | (e2) |
| (27) HOGpApGpCpApTpCpCpApApApApGpApGOH | (e3) |
| (28) HOCpCpTpTpApApApGpTpTpTpTpTpGpAOH | (e4) |
| (29) HOGpGpApTpGpCpTpCpTpGpGpTpCpApTOH | (e5) |
| (30) HOTpCpTpCpCpApApCpApCpTpCpTpTpTOH | (e6) |
| (31) HOTpGpTpGpGpApGpApCpApCpApTpCpApAOH | (f1) |
| (32) HOGpGpApApGpApCpApTpGpApApTpGpTOH | (f2) |
| (33) HOCpApApGpTpTpTpTpCpApApApTpApGOH | (f3) |
| (34) HOTpGpTpCpTpTpCpCpTpTpGpApTpGpGOH | (f4) |
| (35) HOApApApApApCpTpTpGpApApTpTpCpAOH | (f5) |
| (36) HOTpTpTpTpGpTpGpCpTpApTpTpGpAOH | (f6) |
| (37) HOCpApApCpApApApApApGpApApApCpGOH | (g1) |
| (38) HOTpGpApTpGpApCpTpTpCpGpApApApAOH | (g2) |
| (39) HOGpCpTpGpApCpTpApApTpTpApTpTpCOH | (g3) |
| (40) HOApGpTpCpApTpCpApCpGpTpTpTpCpTOH | (g4) |
| (41) HOTpApGpTpCpApGpCpTpTpTpTpCpGpAOH | (g5) |
| (42) HOCpApGpTpApCpCpGpApApApTpApApTOH | (g6) |
| (43) HOGpGpTpApApCpTpGpApCpTpTpGpApAOH | (h1) |
| (44) HOTpGpTpCpCpApApCpGpCpApApApGpCOH | (h2) |
| (45) HOApApTpApCpApTpGpApApCpTpCpApTpCOH | (h3) |
| (46) HOGpTpTpGpGpApCpApTpTpCpApApGpTOH | (h4) |
| (47) HOCpApTpGpTpApTpTpGpCpTpTpGpCOH | (h5) |
| (48) HOApTpCpApCpTpTpGpGpApTpGpApGpTOH | (h6) |
| (49) HOCpApApGpTpGpApTpGpGpCpTpGpApAOH | (i1) |
| (50) HOCpTpGpTpCppCpCpApGpCpApGpCpTOH | (i2) |
| (51) HOApApApApCpApGpGpGpApApGpCpGpAOH | (i3) |
| (52) HOGpGpCpGpApCpApGpTpTpCpApGpCpCOH | (i4) |
| (53) HOCpCpTpGpTpTpTpApGpCpTpGpCpTOH | (i5) |
| (54) HOCpTpApCpGpTpTpTpCpGpCpTpTpCOH | (i6) |
| (55) HOApApApCpGpTpApGpTpCpApGpApApTpGpCOH | (j1) |
| (56) HOTpGpTpTpTpCpApApGpGpTpCpGpApAOH | (j2) |
| (57) HOGpApGpCpApTpCpCpApGpTpApApGOH | (j3) |
| (58) HOTpGpApApApCpApGpCpApTpCpTpGpAOH | (j4) |
| (59) HOGpApTpGpCpTpCpTpTpCpGpApCpCpTOH | (j5) |
| (60) HOGpApTpCpCpTpTpApCpTpGpGOH | (j6) |
| (61) HOTpGpTpGpTpApApTpGpApTpApGOH | (l1) |
| (62) HOTpApCpApCpApCpTpCpTpTpTpTOH | (l2) |
| (63) HOGpApTpCpCpTpApTpCpApTOH | (l3) |

(wherein, Ap is deoxyadenyl, Gp is deoxyguanyl, Cp is deoxycitidyl and Tp is thymidyl).

A. Fra-B-4 (DNA Fragment Encoding LH)

A.1. Ligation of Synthetic Oligonucleotides

Each oligonucleotide (A2 - L2) (each 0.4 nM) was phosphorylated with T4 polynucleotide kinase (BRL; 2.5 U) in 40 μg/ml of ligation buffer (50 mM Tris-HCl, pH 7.6, 20 mM DTT, 50 μg/ml BSA, 1 mM spermidine, 10 mM MgCl₂ and 2 mM ATP) at 37° C. for 3 hours. The reaction mixture was incubated at 100° C. for 5 minutes to inactivate the enzyme. Phosphorylated oligonucleotides were ligated to two oligonucleotides (A1 and L3) in accordance with the procedure illustrated in FIG. 13 (1), to form a DNA fragment encoding LH (236 bp). The ligation reaction was conducted in a reaction mixture containing 1 μl of 50 mM ATP at 16° C. for 5 hours. Each ligation product was separated on 2-16% gradient PAGE (polyacrylamide gel electrophoresis) in Tris-EDTA buffer and visualized by ethidium bromide.

A.2. Cloning of LH-encoding gene

Plasmid pBR322 was digested with BamHI and EcoRI and the reaction was terminated by heating at 65° C. for 5 minutes. The large DNA fragment was isolated on 0.5% agarose gel electrophoresis and ligated to DNA fragment encoding LH in the presence of T4 DNA ligase at 12° C. for 18 hours. The ligated DNA constituted the desired plasmid pLH107. The resultant ligation mixture was used to transform *E. coli* HB101 in substantial accordance with the procedure of Kushner's method (Maniatis, T. et al., Molecular Cloning, pp 252, 1982, Cold Spring Harber Laboratories) and the transformants were selected on agar plate containing 25 μg/ml tetracycline. Ampicillin resistant and tetracycline sensitive clone was selected. The plasmid was isolated from the clone and digested with EcoRI and BamHI, and confirmed the presence of the desired 236 bp LH-encoding gene on the basis of the size of the fragment compared with an appropriate size marker.

The plasmid pLH107 isolated from *E. coli* HB101 transformant was characterized by restriction analysis to contain the DNA fragment encoding LH.

B. Fra-B-5 (DNA Sequence Encoding RH)

B.1. Ligation of Synthetic Oligonucleotides

Each oligonucleotides (D3 - J5) (each 0.4 mM) was phosphorylated in accordance with the procedure described in A.1., and ligated to an oligonucleotide (J6) in accordance with the procedure shown in FIG. 13 (2) to yield a DNA fragment encoding RH (270 bp). The ligation mixture was purified on PAGE to give the 270 bp RH-encoding DNA, which was used for the cloning of LH-RH-encoding DNA.

The synthesis protocol for Fra-B-4 and Fra-B-5 are shown in FIG. 13, (1) and (2).

B.2. Cloning of LH-RH-encoding gene

Fra-B-5 was ligated into the large HindIII-BamHI restriction fragment of plasmid pLH 107 in the presence of T4 DNA ligase. The ligation mixture was used to transform E. coli HB 101 and plasmid pγF-3 was isolated from the transformants. The 450 bp EcoRI-BamHI restriction fragment encoding LH-RH (Fra-B-6) was obtained from the plasmid.

Preparation 2

Synthesis and Cloning of DNA Fragment Encoding Trp Promoter II (Fra-B-1)

Fra-B-1 was synthesized in substantial accordance with the teaching of Preparation 1, and ligated into the EcoRI-BamHI restriction fragment of pBR322, and the ligation mixture was used to transform E. coli HB101. The Amp$^R$ and Tet$^S$ transformant was selected, and the plasmid obtained therefrom was digested with HpaI to identify a 4.1 kbp band, which was then digested with BamHI, and a 90 bp band was confirmed on PAGE. A 56 bp EcoRI-BamHI restriction fragment of said 90 bp DNA fragment was confirmed by PAGE using a size marker. The synthesis protocol for Fra-B-1 is presented in FIG. 14. The oligonucleotides used for the synthesis of Fra-B-1 is as follows.

Fra-B-1 Oligonucleotides for synthetic trp promoter II gene (1) HOApApTpTpTpGpCpCpGpApCpAOH (A)
(2) HOCpGpTpTpApTpGpApTpGpTpCpGpGpCpAOH (B)
(3) HOTpCpApTpApApCpGpGpTpTpCpTpGpTpGpCOH (C)
(4) HOGpApApTpApTpTpTpGpCpCpApGpApApCOH (D)
(5) HOApApApTpApTpTpCpTpGpApApApTpGpAOH (E)
(6) HOTpCpApApCpApGpCpTpCpApTpTpTpCpAOH (F)
(7) HOGpCpTpGpTpTpGpApCpApApTpTpApApTOH (G)
(8) HOGpTpTpCpGpApTpGpApTpTpApApTpTpGOH (H)
(9) HOCpApTpCpGpApApCpTpApGpTpTpApApCOH (I)
(10) HOGpCpGpTpApCpTpApGpTpTpApApCpTpAOH (J)
(11) HOTpApGpTpApCpGpCpApApApGpTpTpCpApCOH (K)
(12) HOCpTpTpTpTpApCpGpTpGpApApCpTpTOH (L)
(13) HOGpTpApApApApApGpGpGpTpApTpCpGOH (M)
(14) HOApApTpTpCpGpApTpApCpCOH (N)

Preparation 3

Construction of Plasmid p322dtrpS Encoding Trp Promoters I and III

A. Construction of Plasmid pBR322trp

Five hundreds nanogram of 375 bp EcoRI-BamHI restriction fragment (Fra-B-2) was isolated from 9 μg of plasmid pBR322 and the fragment (100 ng) was ligated into 200 μg of 4094 bp EcoRI-BamHI restriction fragment of plasmid pTrpEB7 (prepared in Preparation 2) in 20 μl of ligation buffer containing 1 mM ATP and T4 DNA ligase (360 units, Takara Syuzo, Inc.) at 15° C. overnight. The ligation mixture was used to transform E. coli HB101, and Tet$^R$ transformant was selected on agar plate containing 25 μg/ml tetracycline. Plasmid pBR322trp was isolated from the transformant and the presence of the gene encoding trp promoter I was confirmed by EcoRI-BamHI and HpaI digestion, and subsequent 7.5% PAGE and 0.8% agarose gel electrophoresis.

B. Preparation of DNA Fragment Encoding Trp Promoter III (Fra-B-3)

For the preparation of Fra-B-3, following oligonucleotides were synthesized.

Fra-B-3 Oligonucleotides for synthetic trp promoter III gene (1) HOApApTpTpTpGpCpCpGpApCpAOH (A)
(2) HOCpGpTpTpApTpGpApTpGpTpCpGpGpCpAOH (B)
(3) HOTpCpApTpApApCpGpGpTpTpCpTpGpTpCOH (C)
(4) HOGpApApTpApTpTpTpGpCpCpApGpApApCOH (D)
(5) HOApApApTpApTpTpCpTpGpApApApTpGpAOH (E)
(6) HOTpCpApApCpApGpCpTpCpApTpTpTpCpAOH (F)
(7) HOGpCpTpGpTpGpApCpApApTpTpApApTOH (G)
(8) HOGpTpTpCpGpApTpGpApTpTpApApTpTpGOH (H)
(9) HOCpApTpCpGpApApCpTpApGpTpTpApApCOH (I)
(10) HOCpCpGpTpApCpTpApGpTpTpApApCpTpOAH (J)
(11) HOTpApGpTpApCpGpCpApApApGpTpTpCpApCOH (K)
(12) HOCpTpTpTpTpApCpGpTpGpApApCpTpTOH (L)
(13) HOGpTpApApApApApGpGpGpTpApTOH (M')
(14) HOCpGpApTpApCpCOH (N')

Each of oligonucleotides (B-M') (0.2 nM) of blocks I', II', and III' (FIG. 15) was phosphorylated with T4 polynucleotide kinase (2.5 U, BRL) in 70 μl of ligation buffer at 37° C. for 1 hour. To the reaction mixture of each block were added 300 U of T4 DNA ligase and 2 μl of 20 mM ATP, and the mixture was incubated at 15° C. for 30 minutes. The reaction was terminated by heating at 65° C. for 10 minutes. The ligation mixtures of each block were combined and mixed with unphosphorylated oligonucleotides A and N' in the presence of 360 U of T4 DNA ligase and 2 μl of 20 mM ATP. After incubation of the mixture at 15° C. for 1 hour, the final ligation product was purified on 2–16% gradient polyacrylamide gel to give 105 bp trp promoter III-encoding DNA (Fra-B-3).

C. Construction of Plasmid p322dtrpS Encoding...Trp Promoter I and III

Figure 2A:
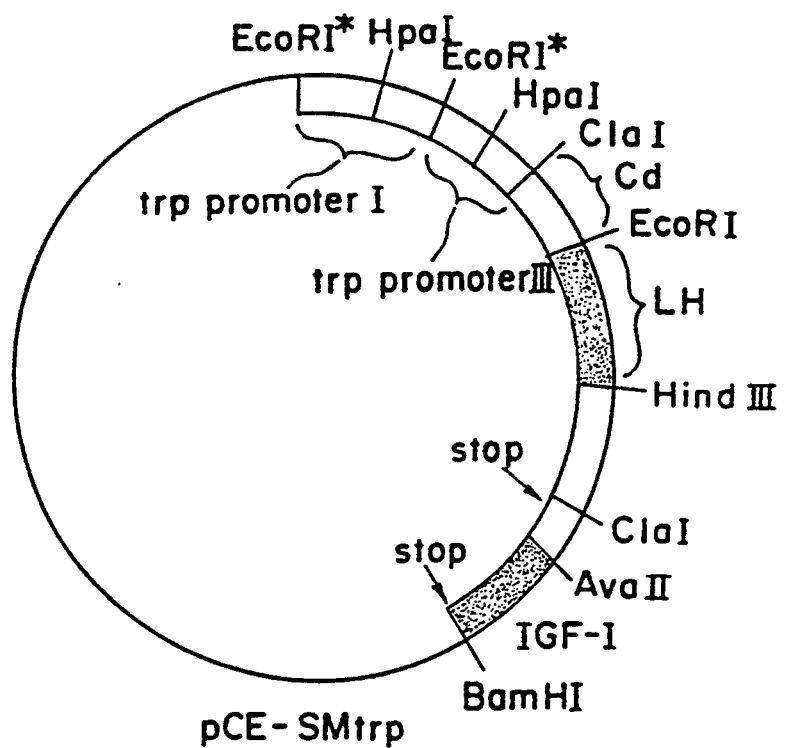
FIG. 2 (1) is a restriction site and functional map of plasmid pCE-SMtrp, and FIG. 2 (2) is a restriction site and functional map of plasmid pCE-SM3t.
Figure 2B:
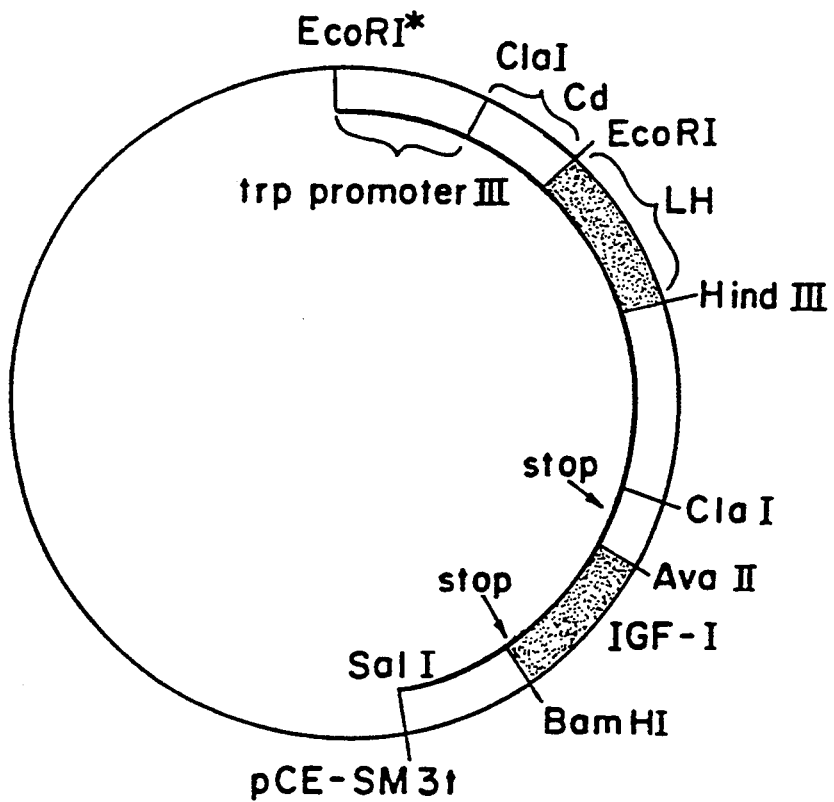
Figure 3:
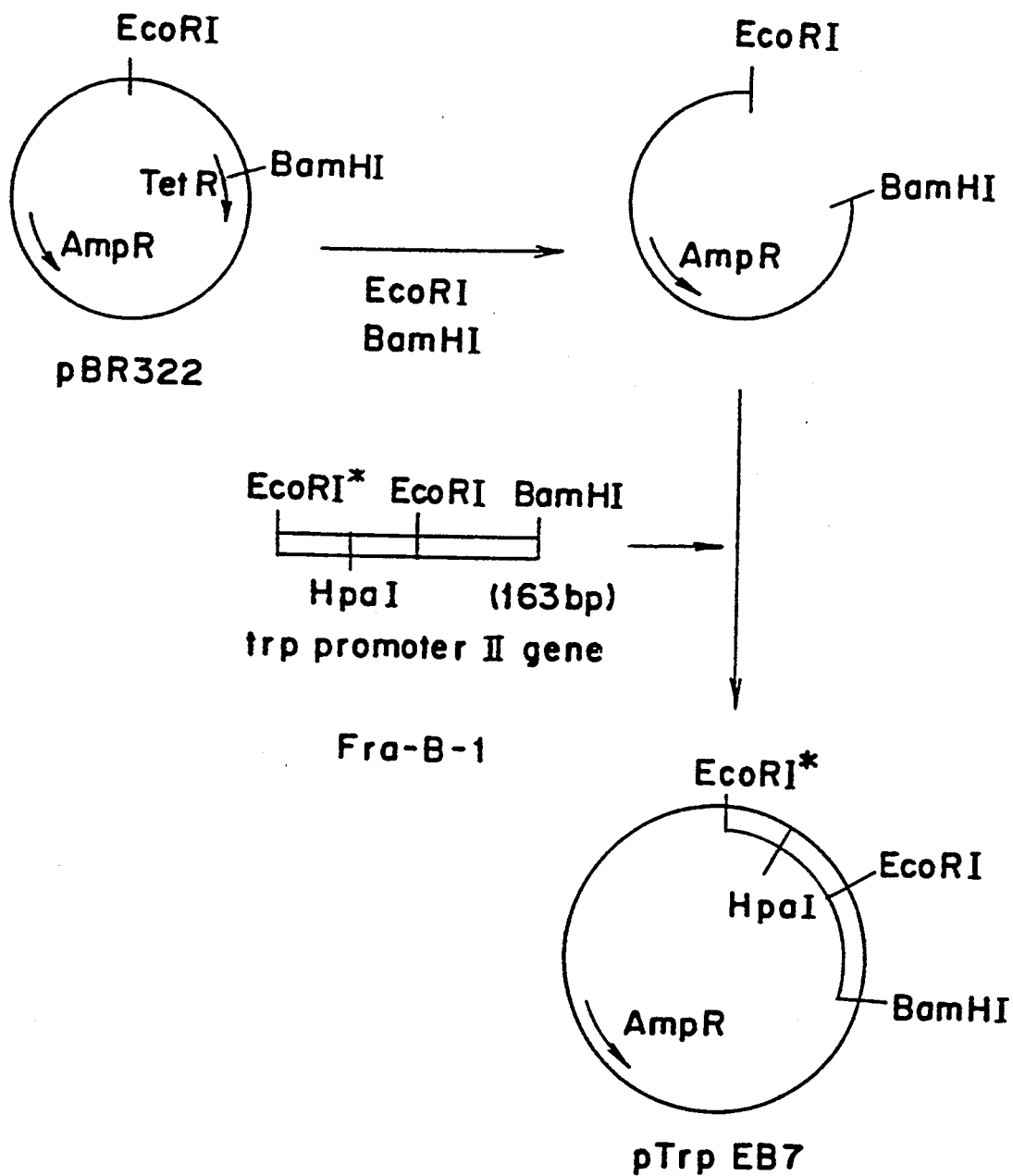
FIG. 3 is a schematic illustration of the construction protocol for plasmid pTrpEB7.
Figure 4:
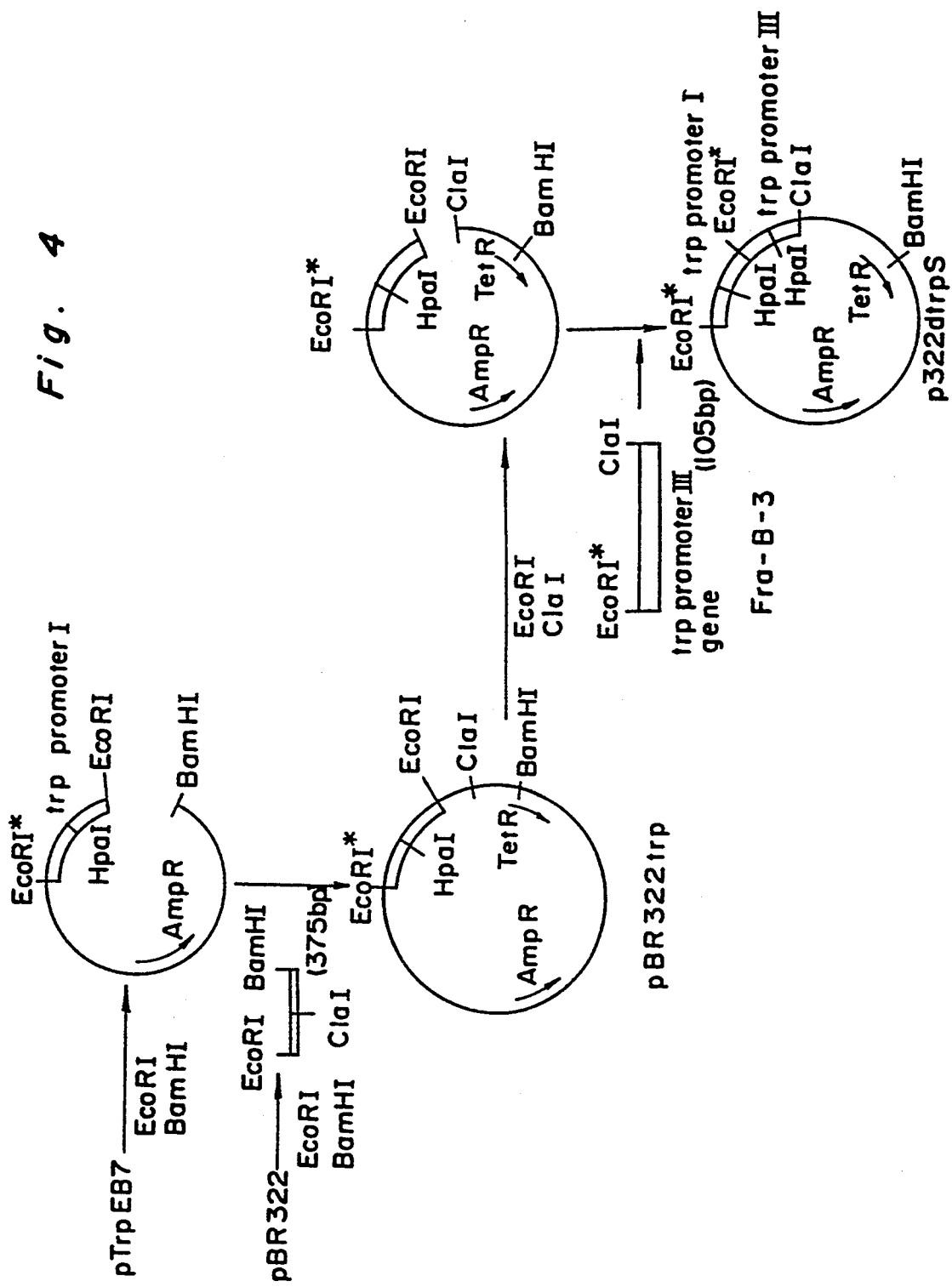
FIG. 4 is a schematic illustration of the construction protocol for plasmid p322dtrpS.

Fra-B-3 was ligated into 4446 bp EcoRI-ClaI restriction fragment of plasmid pBR322trp. The resulting ligation mixture was used to transform E. coli HB101 and ampicillin-resistant and tetracycline-resistant transformants were selected. Plasmid p322 dtrpS was isolated from the transformant and the presence of ClaI-BamHI (352 bp), HpaI (107 bp), and AatII-ClaI (287 bp) restriction fragments were confirmed by restriction analysis. The schematic construction protocol is presented in FIG. 4.

Preparation 4

Construction of Expression Vector pCdγ

A. Construction of LH-RH Expression Vector pγtrp

LH-RH gene (Fra-B-6, prepared in Preparation 1 B.2) was ligated into the 4.1 kbp EcoRI-BamHI restriction fragment of plasmid pTrpEB7 (prepared in Preparation 2). The ligation mixture was used to transform E. coli HB101 and Amp$^R$ and Tet$^S$ transformants were selected. Plasmid pγtrp was isolated from the transformants and the presence of 450 bp EcoRI-BamHI restriction fragment (Fra-B-6) was confirmed on 7.5% PAGE.

B. Construction of Plasmid pCdγ

B.1 Preparation of DNA Fragment Encoding Part of Trp Promoter III and Cd (Fra-B-7)

For the construction of Fra-B-7, the following 18 oligonucleotides were synthesized.

Fra-B-7 Oligonucleotides for peptide Cd gene with a part of DNA fragment of synthetic trp promoter III gene (1) HOApApCpTpApGpTpApCpGpCpCOH (Np1)
(2) HOApApCpTpTpGpCpCpGpTpApCpTpApGpTpTOH (Np4)
(3) HOApApGpTpTpCpCpApCpGpTpApApApApApApGOH (Np2)
(4) HOApTpApCpCpCpTpTpTpTpTpApCpGpTpGOH (Np5)

-continued
(5) HOGpGpTpApTpCpGpApTpApApApApTpGOH (Np3)
(6) HOGpTpApGpApApCpApTpTpTpTpApTpCpGOH (Np6)
(7) HOTpTpCpTpApCpTpTpCpApApCpApApAOH (Cd1)
(8) HOGpGpTpCpGpGpTpTpTpGpTpTpGpApAOH (Cd2)
(9) HOCpCpGpApCpCpGpGpCpTpApTpGOH (Cd3)
(10) HOGpCpTpGpGpApGpCpCpApTpApGpCpCOH (G'2)
(11) HOGpCpTpCpCpApGpCpTpCpTpCpGpTpCOH (H'1)
(12) HOCpGpGpTpGpCpGpCpGpApCpGpApGpAOH (H'2)
(13) HOGpCpGpCpApCpCpGpCpApGpApCpTpGOH (I'1)
(14) HOGpApTpApCpCpApGpTpCpTpGOH (Cd4)
(15) HOGpTpApTpCpGpTpApApGpApCpGOH (Cd5)
(16) HOApCpCpCpTpCpGpTpCpTpApCOH (Cd6)
(17) HOApGpGpGpTpGpGpCpGpApTpGOH (Cd7)
(18) HOApApTpTpCpApTpCpGpCpCOH (Cd8)

Each of oligonucleotides (Np1-Cd8) (0.2 nM) of blocks I'', II'', and III'' (FIG. 16) were phosphorylated with T4 nucleotide kinase (2.5 U, BRL) in 60 μl of ligation buffer at 37° C. for 1 hour. To the reaction mixture of each block were added 360 U of T4 DNA ligase and 2 μl of 20 mM ATP, and the mixture was incubated at 15° C. for 1 hour. The reaction mixtures of each blocks were combined and incubated in the presence of 360 U of T4 DNA ligase and 2 μl of 20 mM ATP overnight at 15° C., and then 10 minutes at 80° C. To the reaction mixture were added 20 μl of 500 mM NaCl and 20 U of EcoRI. After incubation of the mixture at 37° C. for 2 hours, the final ligation product was purified on 15% PAGE to give 124 bp DNA fragment, Fra-B-7. The synthesis protocol for Fra-B-7 is shown in FIG. 16.

B.2 Construction of Plasmid pCdγ

The 124 bp DNA fragment (Fra-B-7) was ligated into the 4510 bp HpaI-EcoRI restriction fragment of plasmid pγtrp. The ligation mixture was used to transform E. coli HB101 and Amp$^R$ transformants were isolated. Plasmid pCdγ was isolated from the Amp$^R$ transformants and the presence of ClaI-BamHI (543 bp), ClaI-HindIII (273 bp), and AatII-ClaI (180 bp) restriction fragments were confirmed by restriction analysis. The schematic construction protocol of said plasmid is represented in FIG. 5.

Preparation 5

Construction and Cloning of Plasmid pCdγtrpSd

Fra-B-8 was isolated from plasmid pCdγ as a 542 bp ClaI-BamHI restriction fragment and ligated into the 4223 bp ClaI-BamHI restriction fragment of plasmid p322dtrpS (Preparation 3.C). The resultant ligation mixture was used to transform E. coli HB101 and Amp$^R$ transformants were selected. Plasmid pCdγtrpSd was isolated from the transformants and the presence of HpaI-BamHI (107 and 575 bp), ClaI-BamHI (543 bp), PstI-EcoRI (1057 bp), EcoRI-BamHI (450 bp), HindIII-BamHI (270 bp) and ClaI-HindIII (273 bp) restriction fragments were confirmed by restriction analysis. The schematic construction protocol of said plasmid pCdγtrpSd is presented in FIG. 6.

Preparation 6

Construction and Cloning of α-hANP-encoding DNA with linker DNA (Fra-B-9)

A. Preparation of a α-hANP-encoding DNA with linker DNA (Fra-B-9)

The ligation and purification procedures for the preparation of Fra-B-9 were conducted in substantial accordance with the method of Preparation 3, B using 300 units of T4 DNA ligase.

For the preparation of Fra-B-9, the following 18 oligonucleotides were synthesized. Oligonucleotides AN1-AH18 were used as starting materials. The synthesis protocol for 134 bp DNA fragment (Fra-B-9) is shown in FIG. 17.

Fra-B-9 Oligonucleotides for α-hANP gene with linker DNA
(1) HOApGpCpTpTpGpApApApGpTpTpGpApGpCpApTpGOH (AH1)
(2) HOApApTpTpCpApTpGpCpTpCpApApCpTpTpCpAOH (AT2)
(3) HOApApTpTpCpGpGpGpTpApTpGpGpGpCOH (AH3)
(4) HOTpTpCpApCpCpGpCpCpCpApTpApCpCpCpGOH (AH4)
(5) HOGpGpTpGpApApGpCpTpApApApTpCpTOH (AH4)
(6) HOCpGpCpApGpApGpApTpTpTpApGpCOH (AH6)
(7) HOCpTpGpCpGpTpApGpApTpCpCpTpCpTOH (AH7)
(8) HOApApGpCpApApGpApGpGpApTpCpTpAOH (AH8)
(9) HOTpGpCpTpTpTpGpGpTpGpGpCpCpGpTOH (AH9)
(10) HOTpCpCpApTpApCpGpGpCpCpApCpCpAOH (AH10)
(11) HOApTpGpGpApCpCpGpGpCpApTpCpGpGTOH (AH11)
(12) HOpTpGpApGpCpApCpCpGpApTpGpCpCpGpGOH (AH12)
(13) HOGpCpTpCpApGpTpCpCpGpGpTpCpTpGOH (AH13)
(14) HOCpApGpGpCpCpApGpApCpCpGpGpApCOH (AH 14)
(15) HOGpGpCpTpGpTpApApCpTpCpTpTpTpCOH (AH15)
(16) HOTpApApCpGpGpApApApApGpApGpTpTpAOH (AH16)
(17) HOCpGpTpTpApCpTpGpApTpApGOH (AH17)
(18) HOGpApTpCpCpTpApTpCpApGOH (AH18)

B. Construction and Cloning of Plasmid pCLaHtrpSd

The 134 bp DNA fragment (prepared in above A.) was ligated into the 4743 bp HindIII-BamHI restriction fragment of plasmid pCdγtrpSd (prepared in Preparation 5). The ligation mixture was used to transform E. coli HB 101 and the Amp$^R$ transformant (E. coli HI) was isolated and used for the preparation of plasmid pCLaHtrpSd which encodes Cd-LH-α-hANP (fused peptide of Cd-LH and α-hANP). The resultant plasmid was subjected to the restriction analysis to confirm the presence of AatII-ClaI (287 bp), ClaI-BamHI (407 bp), ClaI-EcoRI (93 and 198 bp), EcoRI-BamHI (116 and 198 bp), HindIII-BamHI (134 bp) and HpaI-BamHI (107 and 439 bp) restriction fragments. The construction protocol for the plasmid pCLaHtrpSd is presented in FIG. 6.

Preparation 7

Construction of LH Expression Vector pLHtrp

LH gene (Fra-B-4, prepared in Preparation 1,A.2) was ligated into 4.1 kbp EcoRI-BamHI restriction fragment of plasmid pTrpEB7 (prepared in Preparation 2). The ligation mixture was used to transform E. coli HB 101 and Amp$^S$ and Tet$^R$ transformants were obtained. Plasmid pLHtrp was isolated from the transformants and the presence of the 236 bp DNA fragment (Fra-B-6)

was confirmed by EcoRI-BamHI digestion and 7.5% agarose gel electrophresis. The construction protocol is presented in FIG. 7.

Preparation 8

IGF-I Expression Vector pLHSdMmtrp

A. Preparation of Gene Encoding IGF-I (Fra-B-10)

A.1. Ligation of Synthetic Oligonucleotides

For the preparation of Fra-B-10, the following 30 oligonucleotides were synthesized. Oligonucleotides for IGF-I gene, Oligonucleotides for IGF-I gene, Fra-B-10

| | |
|---|---|
| (1) HOApApTpTpCpApTpGpGpGpTOH | (A1) |
| (2) HOTpTpTpCpApGpGpApCpCpCpApTpGOH | (A2) |
| (3) HOCpCpTpGpApApApCpTpCpTpGpTpGOH | (B1) |
| (4) HOCpApGpCpGpCpCpGpCpApCpApGpApGOH | (B2) |
| (5) HOCpGpGpCpGpCpTpGpGpApApCpTpGpGpTOH | (C1) |
| (6) HOApGpApCpGpCpGpTpCpApApCpCpApGpTpTOH | (C2) |
| (7) HOTpGpApCpGpCpTpCpTpGpCpApApTpTpTOH | (D1) |
| (8) HOCpCpApCpApTpApCpApApApApTpTpGpCOH | (D2) |
| (9) HOGpTpApTpGpTpGpGpTpGpApTpCpGpTOH | (E1) |
| (10) HOTpApGpApApApCpCpApCpGpApTpCpAOH | (E2) |
| (11) HOGpGpTpTpTpCpTpApCpTpTpCpApApCOH | (F1) |
| (12) HOGpGpTpCpGpGpTpTpTpGpTpTpGpApApGOH | (F2) |
| (13) HOApApApCpCpGpApCpCpGpGpCpTpApTpGOH | (G1) |
| (14) HOGpCpTpGpGpApGpCpCpApTpApGpCpCOH | (G2) |
| (15) HOGpCpTpCpCpApGpCpTpCpTpCpGpTpCOH | (H1) |
| (16) HOCpGpGpTpGpCpGpCpGpApCpGpApGpAOH | (H2) |
| (17) HOCpGpCpApCpCpGpCpApGpApCpTpGOH | (I1) |
| (18) HOCpTpApCpGpApTpApCpCpApGpTpCpTpGOH | (I2) |
| (19) HOGpTpApTpCpGpTpApGpApCpGpApApTpGOH | (J1) |
| (20) HOGpApApApCpApGpCpApTpTpCpGpTOH | (J2) |
| (21) HOCpTpGpTpTpTpCpGpTpTpCpTpTpGOH | (K1) |
| (22) HOGpGpApGpApTpCpGpCpApApGpApApCOH | (K2) |
| (23) HOCpGpApTpCpTpCpCpGpCpCpGpTpCpTOH | (L1) |
| (24) HOTpApCpApTpTpTpCpCpApGpApCpGpGpCOH | (L2) |
| (25) HOGpGpApApApTpGpTpApCpTpGpTpGpCpTOH | (M1) |
| (26) HOTpTpCpApGpTpGpGpApApGpCpApCpAOH | (M2) |
| (27) HOCpCpApCpTpGpApApGpCpCpApGpCpAOH | (N1) |
| (28) HOGpCpGpGpApTpTpTpGpCpTpGpGpCOH | (N2) |
| (29) HOApApApTpCpCpGpCpGpTpGpApTpApGOH | (O1) |
| (30) HOGpApTpCpCpTpApTpCpApCOH | (O2) |

Each oligonucleotide (A1-O2, FIG. 18) (each 0.4 nM) was phosphorylated with T4 polynucleotide kinase in 100 μl of ligation buffer (74 mM Tris-HCl, pH 7.6, 10 mM DTT, 1.6 mM mercaptoethanol, 10 mM MgCl₂ and 0.5 mM ATP) at 37° C. for 20 minutes. When the reaction was completed, the reaction mixture was incubated at 100° C. for 5 minutes to inactivate the enzyme. In accordance with the process in FIG. 18, the IGF-I-encoding DNA was prepared for cloning. The ligation was conducted in a reaction mixture containing 7 units of T4 DNA ligase and 0.5 μl of 100 mM ATP at 4° C. for 23 hours. Each ligation product was separated by 2–16% gradient PAGE in Tris-EDTA buffer and visualized by ethidium bromide.

A.2. Cloning of 224 bp DNA Fragment Encoding IGF-I

Fra-B-10 was ligated into the 3985 bp BamHI-EcoRI restriction fragment of plasmid pBR322 at 12° C. for 18 hours. The resultant ligation mixture was used to transform E. coli HB101 in substantial accordance with the procedure of Kushner's method (supra) and the Amp$^R$ transformants were selected on agar plate containing 25 μg/ml of tetracycline. The presence of desired 224 bp DNA fragment was confirmed by EcoRI and BamHI digestion of the plasmid which had been isolated from the Amp$^R$ and Tet$^S$ clones and the comparison of the restriction fragments with appropriate size markers.

Desired plasmid, designated pSdM1, was characterized by the existence of Met-IGF-I encoding gene by restriction analysis.

B. Construction of IGF-I Expression Vector pLHSdMtrp

For the preparation of Fra-B-11, the following oligonucleotides were synthesized.

Fra-B-11  IGF-I gene with linker DNA containing internal SD sequence

| | |
|---|---|
| (1) HOApGpCpTpTpGpApApGpTpApApApApCpApTpGOH | (m1) |
| (2) HOApApTpTpCpApTpGpTpTpTpTpApCpTpTpCpAOH | (m2) |

Oligonucleotide m2 was phosphorylated in accordance with the method of Preparation 8.A.1. Phosphorylated oligonucleotide m2 and unphosphorylated oligonucleotide m1 were ligated to the 224 bp EcoRI-BamHI restriction fragment of plasmid pSdM1 (above A.2) with T4 polynucleotide kinase in the ligation buffer containing 100 mM ATP at 4° C. for 20 hours. After digestion with BamHI, the ligation mixture was purified on PAGE to isolate the IGF-I-encoding DNA with linker DNA (242 bp, Fra-B-11). Fra-B-11 was ligated to the HindIII-BamHI restriction fragment of pLHtrp and the ligation mixture was used to transform E. coli HB 101. The host cell containing the transforming plasmid was designated E. coli F-6. From this transformants was isolated plasmid pLHSdMmtrp, and the plasmid was subjected to the restriction analysis. On the 7.5% PAGE, the presence of EcoRI-BamHI (198 and 224 bp), HindIII-BamHI (242 bp) and HpaI-BamHI (456 bp) fragments were confirmed. The construction protocol of said plasmid is presented in FIG. 7. The synthesis protocol of Fra-B-10 is shown in FIG. 18.

Preparation 9

Construction and Cloning of Plasmid pBR322trpSs Encoding Trp Promoter III

Trp promoter III-encoding DNA (prepared in Preparation 3.B.) was ligated into the 4340 bp EcoRI-ClaI restriction fragment of plasmid pBR322 in the presence of 1 mM ATP. The ligation mixture was used to transform E. coli HB 101, and plasmid pBR322trpSs was isolated from the transformants. The presence of HpaI (4445 bp) and ClaI-PstI (834 bp) restriction fragments was confirmed. The schematic construction protocol of said plasmid pBR322trpSs is presented in FIG. 10.

Preparation 10

Construction of Plasmid pCLaHtrp-2

The 406 bp ClaI-BamHI restriction fragment (Fra-C-2) of plasmid pCLaHtrpSd (prepared in Preparation 6.B) was ligated into the 4093 bp ClaI-BamHI restriction fragment of pBR322trpSs (prepared in Preparation 9), and the ligation mixture was used to transform E. coli HB 101. The desired plasmid pCLaHtrp-2 was isolated from the transformants and characterized by restriction analysis: ClaI-PstI (834 bp) and ClaI-BamHI (406 bp). The schematic construction protocol of said plasmid pCLaHtrp-2 is presented in FIG. 10.

Preparation 11

Construction of a α-hANP Expression Vector pCLaHtrp3t bearing Fd Phage Terminator A. Synthesis of Fd Phage Terminator and Cloning thereof Fd phage terminator (Fra-C-1) was synthesized substantially in accordance with the method of Preparation 3.B using following 6 oligonucleotides:

Fra-C-1 Synthetic fd phage terminator gene (1) HOGpApTpCpCpTpCpGpApGpApTpCpApAOH (T1)
(2) HOGpCpCpTpTpTpApApTpTpGpApTpCpTpCpGpApGOH (T2)
(3) HOTpTpApApApGpGpCpTpCpCpTpTpTpTpGpGpAOH (T3)
(4) HOApApApApApGpGpCpTpCpCpApApApApApGpGpAOH (T4)
(5) HOGpCpCpTpTpTpTpTpTpTpTpTpGOH (T5)
(6) HOTpCpGpApCpApApApApAOH (T6)

Oligonucleotides T2, T3, T4 and T5, each 0.4 nM, were mixed and phosphorylated with T4 polynucleotide kinase in the presence of 1 mM ATP. The reaction mixture was incubated at 65° C. for 10 minutes to inactivate the enzyme. To the mixture were added oligonucleotides T1 and T6 (0.8 nM each) and incubated at 15° C. for 30 min in the presence of T4 DNA ligase. The ligation mixture was fractionated on 2–16% gradient polyacrylamide gel, and the desired 47 bp restriction fragment was recovered. The fragment was then ligated into the 4088 bp BamHI-SalI restriction fragment of plasmid pBR322 to form plasmid pter21. Plasmid pter21 was subjected to the restriction analysis to confirm the presence of BamHI-SalI (47 bp) and AvaI (817 bp) restriction fragments.

B. Construction and Cloning of Plasmid pCLaHtrp3t

The 1241 bp PstI-BamHI restriction fragment of plasmid pCLaHtrp-2 (prepared in Preparation 10) was ligated into the 3005 bp PstI-BamHI restriction fragment of plasmid pter21. The resultant ligation mixture was used to transform E. coli HB 101 to give E. coli H2 resistant to ampicillin, from which was isolated plasmid pCLaHtrp3t. The plasmid was then subjected to the restriction analysis to confirm the presence of ClaI-EcoRI (939 and 198 bp), HindIII-BamHI (134 bp), and PstI-ClaI-XhaI (834 and 411 bp) restriction fragments. The schematic construction protocol of plasmid pCLaHtrp3t is presented in FIG. 11.

Example 1

Construction of Met-IGF-I Expression Vector pCE-SMtrp

A. Preparation of Fra-A-7 for the Construction of Two-cistronic Vector

The following oligonucleotides were synthesized for the construction of the DNA fragment.

Fra-A-1 and Fra-A-3 Linker DNA containing internal SD sequence (1) HOGpTpTpGpCpCpApGpTpApCpCpGpCpGpAOH (S)
(2) HOTpTpCpApGpGpTpCpGpCpGpGpTpApCOH (T)
(3) HOCpCpTpGpApApGpCpTpTpGpGpApGpGpAOH (CT1)
(4) HOCpGpApTpTpCpTpCpCpTpCpApApGpCOH (CT2)
(5) HOGpApApTpCpGpApTpApApTpGpTpCpTOH (CT3)
(6) HOCpGpCpApGpApGpApCpApTpTpApTOH (CT4)
(7) HOCpGpApTpApApTpGpGOH (CT5)
(8) HOGpApCpCpCpApTpTpApTOH (CT6)

Oligonucleotides S, T, CT$_1$, CT$_2$, CT$_3$ and CT$_4$ (each 0.4 nM) were phosphorylated with T4 polynucleotide kinase (5 U, Takara Syuzou, Inc.) in 130 μl of ligation buffer (50 mM Tris-HCl, pH 7.6, 20 mM DTT, 1 mM spermidine, 50 μg of BSA, 10 mM MgCl$_2$ and 1 mM ATP) at 37° C. for 1 hour. To the mixture were added 3 μl of 20 mM ATP and 875 units of T4 DNA ligase (Takara Syuzou, Inc.) and the mixture was incubated at 15° C. for 30 minutes, and then at 65° C. for 20 minutes, to inactivate the enzyme. The ligation mixture was incubated at 15° C. for 30 minutes, and then at 65° C. for 20 minutes, to inactivate the enzyme. The ligation mixture containing 46 bp DNA fragment (Fra-A-1) was incubated with 14 μl of 500 mM NaCl and 10 units of ClaI at 37° C. for 2 hours and the resultant mixture was purified on 2–16% gradient PAGE to obtain 300 ng of 35 bp DNA fragment (Fra-A-2).

A.2. Preparation of 44 bp DNA Fragment (Fra-A-3)

Fra-A-2 (300 ng), CT$_5$ (0.4 nM), and CT$_6$ (0.4 nM) were incubated in the presence of 350 units of T4 DNA ligase in 20 μl of ligation buffer at 15° C. for 30 minutes. The ligation mixture was purified by 2.25% agarose gel electrophoresis (2.25% AGE) to give 100 ng of 44 bp DNA Fragment (Fra-A-3).

A.3. Preparation of Fra-A-5

Plasmid pLHSdMmtrp (10 μg, prepared in Preparation 8, 4.5 kbp) was digested with HindIII and BamHI to yield 300 ng of the 242 bp DNA fragment encoding IGF-I (Fra-A-4), which was then cleaved with AvaII to give 100 ng of 215 bp DNA fragment (Fra-A-5).

A.4. Preparation of Fra-A-7

Fra-A-3 (100 ng), Fra-A-5 (100 ng) and 350 units of T4 DNA ligase were incubated overnight in 12 μl of ligation buffer at 4° C. After heating at 65° C. for 10 minutes, the reaction mixture containing Fra-A-6 was treated with 5 units of each of restriction enzymes BamHI and HindIII. The reaction mixture was purified on 2.25% PAGE to recover 30 ng of 238 bp DNA fragment (Fra-A-7).

B. Construction of plasmid pCE-SMtrp

About 5 μg of HindIII-BamHI restriction fragment was isolated from 10 μg of plasmid pCLaHtrpSd (prepared in Preparation 6), and 200 ng of the fragment was ligated to Fra-A-7 in the presence of 350 units of T4 DNA ligase in 20 μl of ligation buffer at 15° C. for 30 minutes. The resultant ligation mixture was used to transform E. coli DH-1. Plasmid pCE-SMtrp was isolated from Amp$^r$ transformants and confirmed the presence of ClaI-EcoRI (93 and 193 bp), EcoRI-HindIII (180 bp), HindIII-BamHI (238 bp), HpaI-BamHI (107 and 544 bp) restriction fragments. The construction protocol is presented in FIG. 9. The plasmid pCE-SMtrp was transformed into E. coli HB 101 to form the transformant E. coli HB 101/pCE-SMtrp.

Example 2

Construction of Plasmid pCE-SM3t

The 238 bp HindIII-BamHI restriction fragment of plasmid pCE-SMtrp (Fra-A-7) was ligated into the 4137 bp HindIII-BamHI restriction fragment of plasmid pCLaHtrp3t (prepared in Preparation 11) and the ligation mixture was used to transform E. coli HB 101. Recombinant plasmid was isolated from the clone of transformant and confirmed the existence of 286 bp ClaI restriction fragment by restriction analysis. The construction protocol of plasmid pCE-SM3t is presented in FIG. 12.

Example 3

Isolation of Met-IGF-I from *E. coli* HB 101/pCE-SMtrp

A. Expression of IGF-I-encoding Gene

A single colony of transformant *E. coli* HB 101/pCE-SMtrp was grown in L medium (5 ml of LA broth) containing 50 μg/ml ampicillin and incubated at 37° C. After 8 hours cultivation, the culture was added to 100 ml of LA medium and incubated overnight at 37° C. The overnight culture (20 ml) was added to 400 ml of M9CA medium (0.5% casamino acid, 0.2% glucose, 50 μg/ml thiamine HCl, and 25 μg/ml ampicillin) and incubated at 37° C. until the optical density (600 nanometers, A 600) reached 0.5 absorbance unit. To the medium was added 2 ml of IAA (2 mg indoleacrylic acid / ml ethanol), and the culture was incubated for further 3 hours (final A 600=1.40), followed by centrifugation at 6,000 rpm for 5 minutes to collect the cells.

B. Isolation and Purification of Protein

Collected wet cells were resuspended in 8 ml of 10 mM PBS-EDTA buffer (containing 8.0 g NaCl, 0.2 g KCl, 2.9 g Na$_2$HPO$_4$.12H$_2$O, 0.2 g KH$_2$PO$_4$, 3.73 g EDTA in 1L and adjusted pH 8.0 with NaOH) and disrupted by ultrasonification, and the resultant suspension was centrifuged at 15,000 rpm for 20 minutes at 4° C. The supernatant was discarded and the precipitate was resuspended in Gn-HCl buffer (6M guanidine HCl, 10 mM PBS-EDTA, 2 mM β-mercaptoethanol), and the suspension was ultrasonificated at 0° C. After centrifugation of the suspension at 15,000 rpm at 4° C. for 20 min, the supernatant was dialyzed 3 times against each 1000 ml of 1M AcOH. Thirty ml of acetone was then added to the dialysed solution and the mixture was allowed to stand for 10 min at −78° C. followed by centrifugation at 15,000 rpm for 20 minutes at 4° C. The resultant precipitate was dried under reduced pressure to give crude Met-IGF-I, which was then dissolved in Gn.HCl buffer containing 10% β-mercaptoethanol, and the solution was subjected to the reverse HPLC for further purification (column; Beckman RPSC: flow rate; 1 ml/min: eluent; 0.08% trifluoroacetic acid (TFA) - 10%

$$CH_3CN \xrightarrow{50 \text{ min}}$$

0.08% TFA - 60% CH$_3$CN: wave length: 214 nm).

Yield = 1.6 mg.

C. Identification of Expressed Protein

The purified protein was identified as Met-IGF-I by N-terminal analysis and peptide mapping of the protein which had been treated with chymotrypsin.

What is claimed is:

1. A recombinant DNA expression vector for the production in *Escherichia coli* (*E. coli*) of methionyl insulin-like growth factor I (Met-IGF-I), said vector comprising, in the 5′ to 3′ direction:
    (a) a promoter;
    (b) a first cistron comprising a gene encoding a protective peptide of the formula:

Met Phe Tyr Phe Asn Lys Pro Thr Gly Tyr Gly Ser
   Ser Ser Arg Arg Ala Pro Gln Thr Gly Ile Val Asp Glu Gly Gly
   Asp Glu Phe Met Cys Tyr Cys Gln Asp Pro Tyr Val Lys Glu Ala
   Glu Asn Leu Lys Lys Tyr Phe Asn Ala Gly His Ser Asp Val Ala
   Asp Asn Gly Thr Leu Phe Leu Gly Ile Leu Lys Asn Trp Lys Glu
   Glu Ser Asp Arg Lys Ile Met Gln Ser Gln Ile Val Ser Phe Tyr
   Phe Lys Leu Glu Glu Asn Arg, said gene containing a translational initiation signal immediately adjacent to the codon encoding the N-terminal amino acid of said protective peptide and a translational termination signal positioned downstream from the codon encoding the C-terminal amino acid of said protective peptide;
   (c) a second cistron comprising a gene encoding Met-IGF-I, said gene containing a translational initiation signal immediately adjacent to the codon encoding the N-terminal amino acid of Met-IGF-I and a translational termination signal downstream from the codon encoding the C-terminal amino acid of Met-IGF-I;
   wherein the promoter is operably linked to the first cistron, said vector contains a first Shine-Dalgarno (SD) sequence located upstream from the codon encoding the N-terminal amino acid of said protective peptide and a second Shine-Dalgarno (SD) sequence located upstream from the codon encoding the N-terminal amino acid of said Met-IGF-I, and said vector is selectable and autonomously replicable in *E. coli*.

2. The vector of claim 1 in which the translational termination signal contained in the first cistron and the translational initiation signal contained in the second cistron overlap, or are immediately adjacent to each other, or are separated by one or two intervening nucleotides.

3. The vector of claim 1 in which the promoter is a tryptophan operon promoter.

4. The vector of claim 3 in which the nucleotide sequence of the translational termination signal in the first cistron and the translational initiation signal in the second cistron overlap, and the overlapping sequence is TAATG, wherein A is deoxyadenylate, G is deoxyguanylate, and T is deoxythymidylate.

5. The vector of claim 1 in which the translational termination signal of the second cistron is derived from plasmid pBR322 or fd phage.

6. The vector of claim 1 said vector being a plasmid.

7. A recombinant DNA expression vector for the production in *Escherichia coli* (*E. coli*) of methionyl insulin-like growth factor I (Met-IGF-I), consisting essentially of a plasmid selected from the group consisting of pCE-SMtrp and pCE-SM3t.

8. A method for preparing Met-IGF-I, which comprises:
    (a) transforming *Escherichia coli* with a vector as claimed in any one of claims 1, 7 and 2-6;
    (b) growing said transformed *Escherichia coli* under conditions suitable for expression;
    (c) lysing the transformed *Escherichia coli*; and
    (d) isolating Met-IGF-I from the lysate.

9. A transformed *Escherichia coli* cell containing the vector of claim 1, 7, 2, 3, 4, 5 or 6.

10. The transformed host cell of claim 9 which is *E. coli* HB 101.

* * * * *

UNITED STATES PATENT AND TRADEMARK OFFICE
CERTIFICATE OF CORRECTION

PATENT NO. : 5,340,725
DATED : August 23, 1994
INVENTOR(S) : Ikuo UEDA, et al.

It is certified that error appears in the above-indentified patent and that said Letters Patent is hereby corrected as shown below:

On the title page, Item [75], the fifth inventor's name should be spelled:
--Tadashi Kitaguchi--

Signed and Sealed this

Thirteenth Day of December, 1994

*Attest:*

BRUCE LEHMAN

*Attesting Officer*      *Commissioner of Patents and Trademarks*